US005834460A

United States Patent [19]

Noda et al.

[11] Patent Number: 5,834,460

[45] Date of Patent: Nov. 10, 1998

[54] SERINE DERIVATIVE

[75] Inventors: Ichio Noda; Masahiro Iwata; Shuichi Sakamoto; Kazuo Koshiya; Takuma Morita, all of Ibaraki; Atsuyuki Kohara, Chiba, all of Japan

[73] Assignee: Yamanouchi Pharmaceutical Co., Ltd., Tokyo, Japan

[21] Appl. No.: 535,047

[22] PCT Filed: Apr. 26, 1994

[86] PCT No.: PCT/JP94/00697

§ 371 Date: Oct. 12, 1995

§ 102(e) Date: Oct. 12, 1995

[87] PCT Pub. No.: WO94/25450

PCT Pub. Date: Nov. 10, 1994

[30] Foreign Application Priority Data

| | | | |
|---|---|---|---|
| Apr. 27, 1993 | [JP] | Japan | 5-123454 |
| Sep. 22, 1993 | [JP] | Japan | 5-236428 |

[51] Int. Cl.[6] ........................ H61K 31/445; H61K 31/55; C07D 407/06; C07D 409/04

[52] U.S. Cl. .......................... 514/212; 514/210; 514/326; 514/422; 514/444; 514/471; 540/480; 540/496; 546/212; 546/213; 546/214; 548/517; 548/527; 548/950

[58] Field of Search .................................... 540/596, 480; 514/212, 210, 326, 422, 444, 471; 546/212, 214; 548/517, 527, 950

[56] References Cited

U.S. PATENT DOCUMENTS

| | | | |
|---|---|---|---|
| 4,382,929 | 5/1983 | Bradshaw et al. | 424/246 |
| 5,466,691 | 11/1995 | Nakao et al. | 514/254 |

FOREIGN PATENT DOCUMENTS

| | | |
|---|---|---|
| 0446798 | 9/1991 | European Pat. Off. . |

OTHER PUBLICATIONS

Sice, "*Preparation and Reactions of 2–Methoxythiopene*," Journal of American Chemical Society, vol. 75, pp. 3697–3700 (1953).

Yamada et al., "*Separation of peptide diastereomers by reversed–phase high–performance liquid chromatography and its application*," Journal of Chromatography, vol, 515, pp. 475–482 (1990).

Nakajima et al., "*The Utility of 4–(2–Thienyl)Pyridines as a Derivatization Reagent for HPLC and Ce*," Analytical Sciences, vol. 7, pp. 177–180 (1991).

Nakao, Chemical Abstract 119:2498252 (1993) for WO 93/03025 (Feb. 18, 1983).

Pfizer, Chemical Abstract 93:220595h for JP 80–55143 (Apr. 22, 1980).

*Primary Examiner*—Richard L. Raymond
*Attorney, Agent, or Firm*—Sughrue, Mion, Zinn, Macpeak & Seas, PLLC

[57] ABSTRACT

A serine derivative represented by the general formula (I)

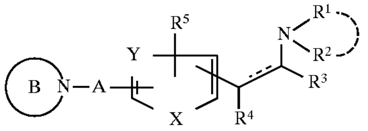

(I)

(symbols in the formula represent the following meanings;

X: a sulfur atom or an oxygen atom,

Y: a nitrogen atom or CH, $R^1$ and $R^2$: the same or different from each other and each represents a hydrogen atom, a lower alkyl group or a protecting group for the amino group, or $R^1$ and $R^2$ may be combined together to form a four- to nine-membered nitrogen-containing cycloalkyl group, $R^3$: a hydrogen atom, a carboxyl group, a protected carboxyl group, an aralkyl group, or a lower alkyl group unsubstituted or substituted with a hydroxyl group, $R^4$: a hydrogen atom or a hydroxyl group, $R^5$: a hydrogen atom or a lower alkyl group, A: a lower alkylene group, B: 1) a saturated or unsaturated four- to ten-membered nitrogen-containing cycloalkyl group unsubstituted or substituted with a lower alkyl group or an aralkyl group or

2) a bicyclic nitrogen-containing hydrocarbon ring radical resulting from the condensation of a four- to eight-membered nitrogen-containing cycloalkyl group with a benzene ring, and . . . : a single or double bond) or a pharmaceutically acceptable salt thereof, which has an anti-PCP (phencyclidine) action and is useful as a psychotropic drug.

9 Claims, No Drawings

SERINE DERIVATIVE

This is a 371 of PCT/JP94/00697, filed Apr. 26, 1994.

TECHNICAL FIELD

This invention relates to a serine derivative which has an anti-PCP (phencyclidine) action.

BACKGROUND ART

It is known that PCP induces mental symptoms which closely resemble various symptoms of schizophrenia including negative symptoms [*Am. J. Psychiat.*, 135, 1081 (1987)]. On the other hand, administration of PCP into animals induces various types of abnormal behavior. Accordingly, a drug which specifically inhibits the PCP-induced abnormal behavior in animals (a drug having anti-PCP action) is considered to be useful as a therapeutic drug for schizophrenia in human.

Dopamine receptor blocking drugs have mainly been used as therapeutic drugs for schizophrenia. These dopamine blocking drugs, however, have problems in that not only their effect against negative symptoms is low but also they cause side effects such as extrapyramidal syndrome.

On the contrary, the specific anti-PCP drug is excellent in that it can improve negative symptoms of schizophrenia, which cannot be cured by the dopamine blocking drugs and that it does not cause side effects which exist in the dopamine blocking drugs.

DISCLOSURE OF THE INVENTION

The inventors of the present invention have conducted intensive studies on the development of a compound having excellent and specific anti-PCP action and, as the result, accomplished the present invention by creating a nitrogen-containing cycloalkyl lower alkyl group-substituted thienyl, furyl or thiazolyl serine derivative, or salts thereof, whose chemical structure is completely different from those of the prior art compounds. Though an unsubstituted thienyl serine derivative (*J. Chromatogr.*, 515, 475–82), a 5-pyridylthienyl serine derivative [*Anal. Sci.*, 7 (Suppl., Proc. Int. Congr. Anal. Sci., 1991, Pt. 1), 177–80] and 5-alkylthienyl or 5-phenylhexylthienyl serine derivative (EP-A-446798) are known in the art as thienyl serine derivatives, these reports do not disclose anti-PCP action of the derivatives.

According to the present invention, there is provided a serine derivative represented by the general formula (I)

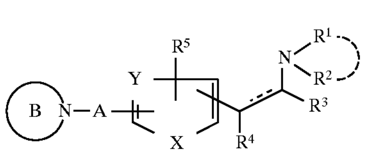

(I)

(symbols in the formula represent the following meanings;

X: a sulfur atom or an oxygen atom,

Y: a nitrogen atom or CH, $R^1$ and $R^2$: the same or different from each other and each represents a hydrogen atom, a lower alkyl group or a protecting group for the amino group, or $R^1$ and $R^2$ may be combined together to form a four- to nine-membered nitrogen-containing cycloalkyl group, $R^3$: a hydrogen atom, a carboxyl group, a protected carboxyl group, an aralkyl group, or a lower alkyl group unsubstituted or substituted with a hydroxyl group, $R^4$: a hydrogen atom or a hydroxyl group, $R^5$: a hydrogen atom or a lower alkyl group, A: a lower alkylene group, B: 1) a saturated or unsaturated four- to ten-membered nitrogen-containing cycloalkyl group unsubstituted or substituted with a lower alkyl group or an aralkyl group or 2) a bicyclic nitrogen-containing hydrocarbon ring radical resulting from the condensation of a four- to eight-membered nitrogen-containing cycloalkyl group with a benzene ring, and ... : a single or double bond) or a pharmaceutically acceptable salt thereof.

In the general formula (I), a serine derivative represented by the following general formula (Ia) or a pharmaceutically acceptable salt thereof is preferable.

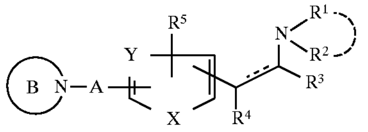

(Ia)

(symbols in the formula represent the following meanings;

X: a sulfur atom or an oxygen atom,

Y: a nitrogen atom or CH, $R^1$: a hydrogen atom, a lower alkyl group, a lower alkoxycarbonyl group, an acyl group, an aralkyl group, an aralkyloxycarbonyl group or an aralkylaminocarbonyl group, $R^2$: a hydrogen atom or a lower alkyl group where $R^1$ and $R^2$ may be combined together to form a four- to nine-membered nitrogen-containing cycloalkyl group, $R^3$: a hydrogen atom, a carboxyl group, a lower alkoxycarbonyl group, an aralkyl group or a lower alkyl group unsubstituted or substituted with a hydroxyl group, $R^4$: a hydrogen atom or a hydroxyl group, $R^5$: a hydrogen atom or a lower alkyl group, A: a lower alkylene group, B: 1) a saturated or unsaturated four- to ten-membered nitrogen-containing cycloalkyl group unsubstituted or substituted with a lower alkyl group or an aralkyl group or 2) a bicyclic nitrogen-containing hydrocarbon ring radical resulting from the condensation of a four- to eight-membered nitrogen-containing cycloalkyl group with a benzene ring, and ... : a single or double bond).

The compound of the above general formula (Ia) wherein X is a sulfur atom and Y is CH, i.e., a serine derivative represented by the following general formula (II) or a pharmaceutically acceptable salt thereof is more preferable.

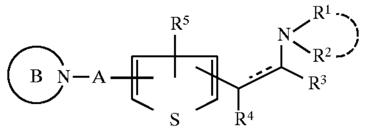

(II)

The compound of the above general formula (II) wherein $R^2$ is a hydrogen atom, B is a saturated or unsaturated four- to ten-membered nitrogen-containing cycloalkyl group unsubstituted or substituted with an aralkyl group and ... is a single bond, i.e., a serine derivative represented by the following general formula (III) or a pharmaceutically acceptable salt thereof is the most preferable.

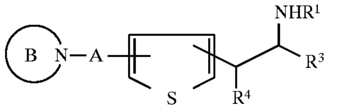

(III)

The following describes the compounds (I), (Ia), (II) and (III) of the present invention in detail.

Unless otherwise noted, the term "lower" as used herein in the definition of the general formulae means a straight or branched carbon chain having 1 to 6 carbon atoms.

Illustrative examples of the "lower alkyl group" include methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, hexyl, isohexyl and the like. Of these groups, those having 1 to 3 carbon atoms, including methyl, ethyl and isopropyl are preferred.

The "protecting group for the amino group" means a protecting group generally used by those skilled in the art, and as its typical examples there are acyl-type protecting groups, for example, lower alkanoyl groups, lower alkoxycarbonyl groups, lower alkanesulfonyl groups such as methanesulfonyl, ethanesulfonyl or the like and aliphatic or aromatic acyl groups such as acetyl, methoxyacetyl, propionyl, butylyl, isobutylyl, valeryl, isovaleryl, pivaloyl, hexanoyl, benzoyl or the like. Illustrative examples for aralkyl-type protecting groups include benzyl, p-methoxybenzyl (to be referred to as "PMB" hereinafter), benzhydryl, trityl and the like. Illustrative examples for carbamate-type protecting groups include benzyloxycarbonyl, p-nitrobenzyloxycarbonyl, p-methoxybenzyloxycarbonyl and the like. Illustrative examples for urea-type protecting groups include benzylaminocarbonyl, p-methoxybenzylaminocarbonyl and the like. Also useful are tri-lower alkylsilyl groups such as trimethylsilyl and the like.

Preferred examples among these groups are lower alkoxycarbonyl groups and aralkyloxycarbonyl groups as carbamate-type protecting groups, aralkylaminocarbonyl groups as a urea-type protecting group and benzyl, phenetyl, phenylpropyl and the like as aralkyl-type protecting groups.

Illustrative examples of the "lower alkoxycarbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyl(amyl)oxycarbonyl, isopentyl(amyl) oxycarbonyl, hexyloxycarbonyl, isohexyloxycarbonyl and the like.

With regard to the "acyl group", aliphatic or aromatic carboxylic acid residues such as lower alkanoyl groups or arylcarbonyl groups may be used, and illustrative examples of the lower alkanoyl group include formyl, acetyl, propionyl, butylyl, isobutylyl, valeryl, isovaleryl, pivaloyl, hexanoyl and the like, of which acetyl group is preferred. Illustrative examples of the arylcarbonyl group include benzoyl, naphthoyl and the like, preferably benzoyl group. Particularly, the benzoyl group may be substituted at optional positions with one or two of a nitro group, a halogen atom, the aforementioned lower alkyl group or a lower alkoxy group, wherein illustrative examples of the halogen atom include fluorine, chlorine, bromine and the like and illustrative examples of the lower alkoxy group include methoxy, ethoxy, propoxy, isopropoxy, butoxy, isobutoxy, tert-butoxy, pentyloxy, hexyloxy and the like.

The "aralkyl group" is a group derived from the aforementioned "lower alkyl group" by substituting its optional hydrogen atom with a carbon ring aryl group such as phenyl, naphthyl or the like, and its illustrative examples include benzyl, phenetyl, phenylpropyl, methylphenylethyl, phenylbutyl, methylphenylpropyl, ethylphenylethyl, dimethylphenylethyl, phenylpentyl, methylphenylbutyl, phenylhexyl, methylphenylpentyl, naphthylmethyl, naphthylethyl, naphthylpropyl, naphthylbutyl, naphthylpentyl, naphthylhexyl and the like.

The "aralkyloxycarbonyl group" is a group in which the aforementioned lower alkoxycarbonyl group is substituted at its optional position with an aryl group such as phenyl, nitrophenyl, a halogenophenyl, a lower alkylphenyl, a lower alkoxyphenyl, naphthyl or the like, and its illustrative examples include benzyloxycarbonyl, phenetyloxycarbonyl, phenylpropoxycarbonyl, phenylbutoxycarbonyl, chlorobenzyloxycarbonyl, fluorobenzyloxycarbonyl, bromobenzyloxycarbonyl, nitrobenzyloxycarbonyl, methylbenzyloxycarbonyl, ethylbenzyloxycarbonyl, propylbenzyloxycarbonyl, methoxybenzyloxycarbonyl, ethoxybenzyloxycarbonyl, propoxybenzyloxycarbonyl and the like.

The term "aralkylaminocarbonyl group" is a group in which the aminocarbonyl group is substituted with one of the aforementioned aralkyl groups, and its illustrative examples include benzylaminocarbonyl, phenetylaminocarbonyl, phenylpropylaminocarbonyl, phenylbutylaminocarbonyl, phenylpentylaminocarbonyl, phenylhexylaminocarbonyl, naphthylmethylaminocarbonyl and the like, of which benzylaminocarbonyl group, phenetylaminocarbonyl group and phenylpropylaminocarbonyl group are preferred.

Examples of the "protected carboxyl group" include lower alkoxycarbonyl groups, aralkyloxycarbonyl groups, lower alkanoyloxyalkoxycarbonyl groups and the like, preferably the aforementioned lower alkoxycarbonyl group.

Particularly preferred are methoxycarbonyl, ethoxycarbonyl, propoxycarbonyl and tert-butoxycarbonyl.

The term "hydroxyl group-substituted lower alkyl group" means a group in which hydroxyl group is substituted at an optional position of the aforementioned lower alkyl group, such as hydroxymethyl, 2-hydroxyethyl, 3-hydroxypropyl, 4-hydroxybutyl, 5-hydroxypentyl, 6-hydroxyhexyl and the like. Unsubstituted lower alkyl groups are as defined in the foregoing.

The term "lower alkylene group" means a straight or branched hydrocarbon chain, and its illustrative examples include methylene, ethylene, methylmethylene, trimethylene, methylethylene, tetramethylene, methyltrimethylene, pentamethylene, hexamethylene, methylpropylene and the like.

The "four- to nine-membered nitrogen-containing cycloalkyl group" formed by $R^1$ and $R^2$ in combination, the "saturated or unsaturated four- to ten-membered nitrogen-containing cycloalkyl group unsubstituted or substituted with a lower alkyl group or an aralkyl group" and the "nitrogen-containing cycloalkyl group" which constitutes the "bicyclic nitrogen-containing hydrocarbon ring radical resulting from the condensation of a four- to eight-membered nitrogen-containing cycloalkyl group with a benzene ring" are nitrogen-containing cycloalkyl groups which contain one to two nitrogen atoms or an oxygen or sulfur atom in addition to the nitrogen atom(s), and illustrative examples of their saturated forms include azetidinyl, pyrrolidinyl, piperidinyl, methylpiperidinyl, ethylpiperidinyl, homopiperidinyl, hexahydroazepinyl, octahydroazoninyl, decahydroazepinyl, homopiperazinyl, morpholinyl, thiomorpholinyl and the like.

Examples of the unsaturated nitrogen-containing cycloalkyl group are the just described groups which further contain one to several double bonds, of which 1,2,3,6-tetrahydropyridinyl is particularly preferred.

Examples of the "bicyclic nitrogen-containing hydrocarbon ring radical resulting from the condensation of a four- to eight-membered nitrogen-containing cycloalkyl group with a benzene ring" include compounds of the following formulae.

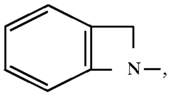, 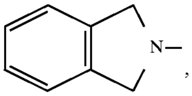,

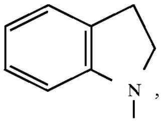, 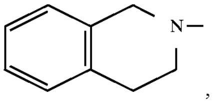,

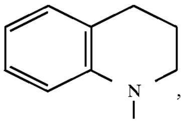, 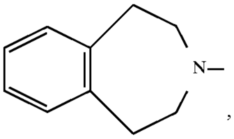,

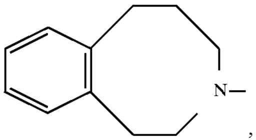,

In some cases, the compound of the present invention may form a salt with an acid or a base. Illustrative examples of salts with acids include acid addition salts with mineral acids such as hydrochloric acid, hydrobromic acid, sulfuric acid, nitric acid, phosphoric acid and the like or with organic acids such as formic acid, acetic acid, propionic acid, oxalic acid, malonic acid, succinic acid, fumaric acid, maleic acid, lactic acid, malic acid, citric acid, tartaric acid, carbonic acid, picric acid, methanesulfonic acid, ethanesulfonic acid, glutamic acid and the like.

Examples of salts with bases include addition salts with inorganic bases such as lithium, sodium, potassium, magnesium, calcium, aluminum and the like or with organic bases such as methylamine, ethylamine, ethanolamine and the like, salts with basic amino acids such as lysine, ornithine and the like and ammonium salt.

The compound of the present invention forms stereoisomers such as tautomers, optical isomers, optically active substances and the like when it contains asymmetric carbon atoms or oxo groups, or generates geometrical isomerism such as cis form, trans form and the like when it contains double bonds. Mixtures and isolated products of these isomers are included in the compound of the present invention.

Also, the compound of the present invention can form a hydrate or a solvate with methanol, ethanol or the like. Thus, the compound of the present invention has been described in detail, and typical examples of the compound to be included in the present invention are shown in Tables 1 to 3, in addition to those described later in Examples.

TABLE 1

| | | | |
|---|---|---|---|
| 1 | 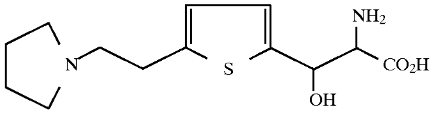 | 8 | 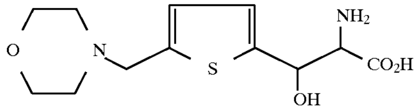 |
| 2 | 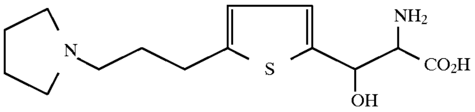 | 9 | 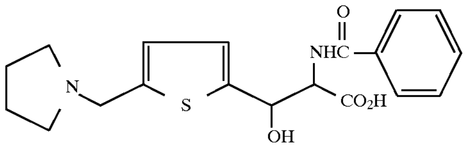 |
| 3 | 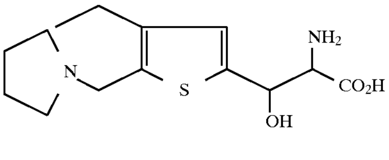 | 10 | 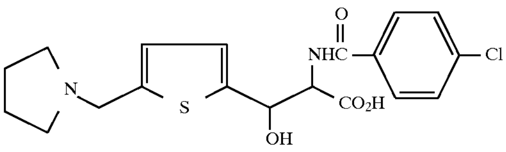 |
| 4 | 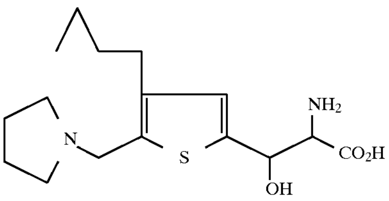 | 11 | 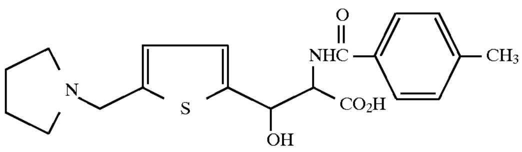 |

TABLE 1-continued
| | | | |
|---|---|---|---|
| 5 | 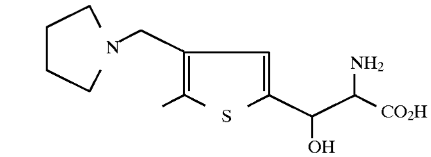 | 12 | 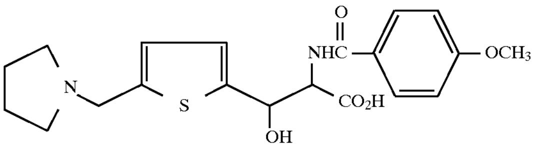 |
| 6 | 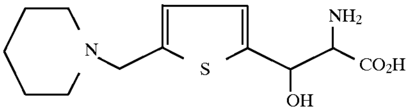 | 13 | 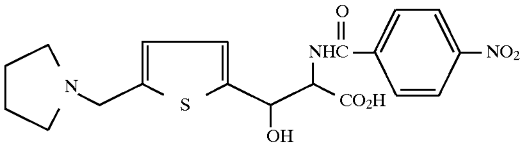 |
| 7 | 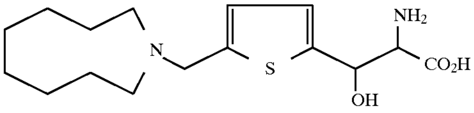 | 14 | 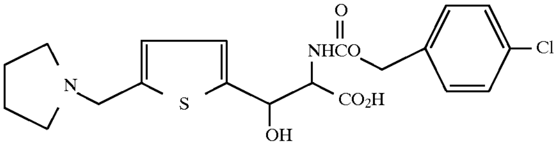 |
TABLE 2
| | | | |
|---|---|---|---|
| 15 | 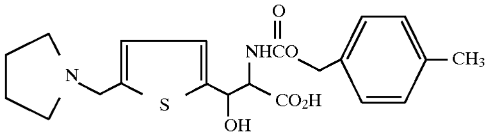 | 22 | 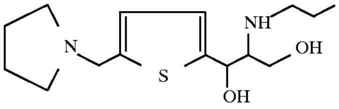 |
| 16 | 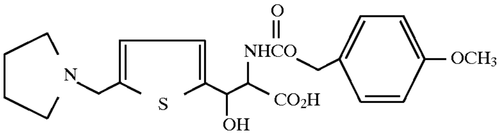 | 23 | 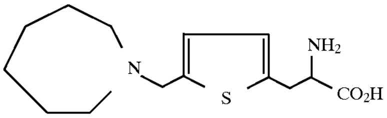 |
| 17 | 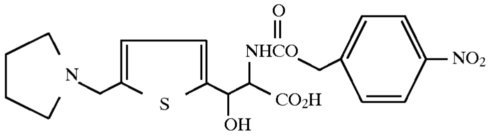 | 24 | 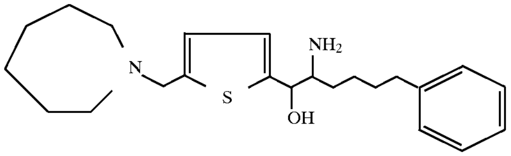 |
| 18 | 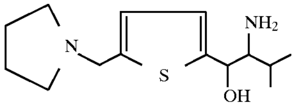 | 25 | 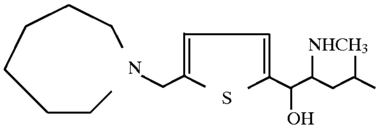 |
| 19 | 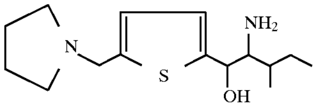 | 26 | 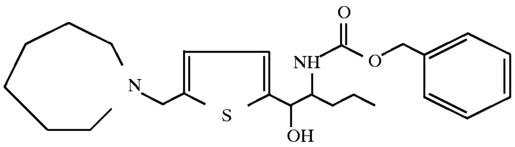 |
| 20 | 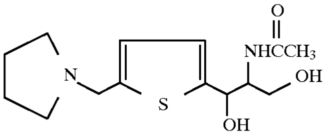 | 27 | 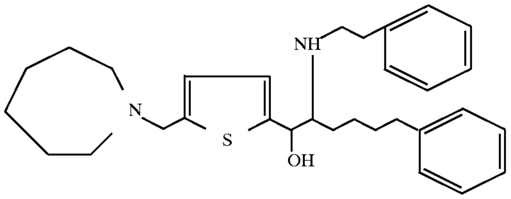 |

TABLE 2-continued

| | | | |
|---|---|---|---|
| 21 | 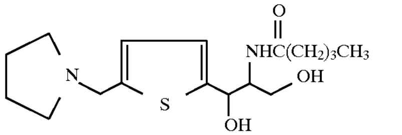 | 28 | 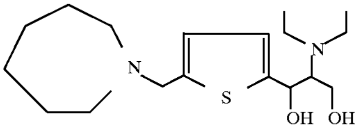 |

TABLE 3

| | | | |
|---|---|---|---|
| 29 | 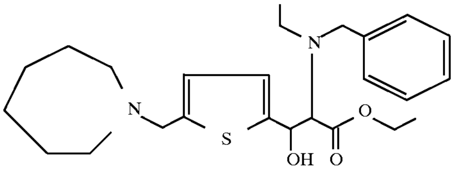 | 32 | 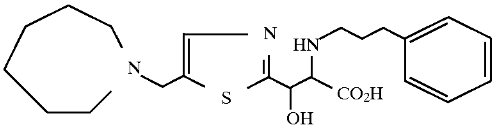 |
| 30 | 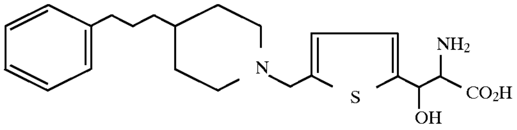 | 33 | 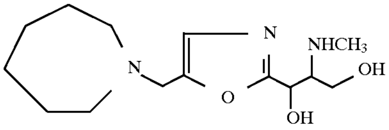 |
| 31 | 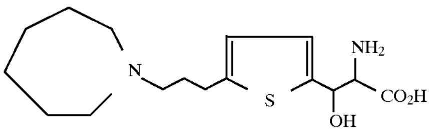 | 34 | 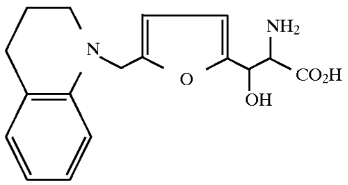 |

(Production methods)

The compound of the present invention can be produced by applying various synthesis methods. The following describes examples of typical production methods. Production method 1

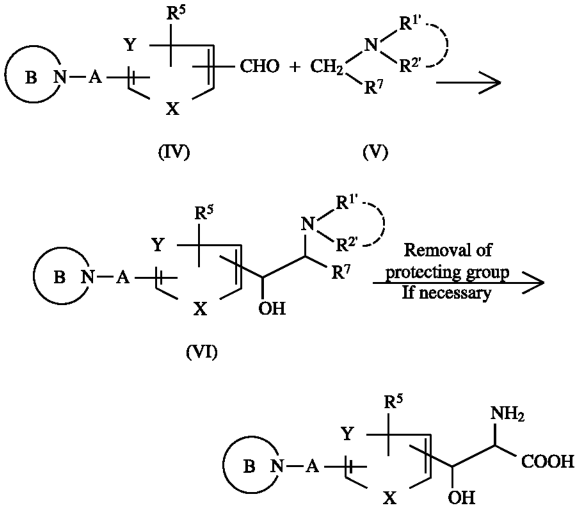

(IV) (V) (VI) (VII)

(In the above formulae, X, Y, $R^5$, A and B are as defined in the foregoing, $R^{1'}$ is one of the groups of $R^1$ except for a hydrogen atom and a lower alkyl group or a protecting group for the amino group and $R^{2'}$ represents a hydrogen atom, a lower alkyl group, an acyl group or an aralkyl group. In this case, the aralkyl group is limited to an arylmethyl group such as benzyl group or the like. $R^{1'}$ and $R^{2'}$ may be combined together to form a four- to nine-membered nitrogen-containing cycloalkyl group. $R^7$ is a lower alkoxycarbonyl group as a member of the groups of $R^3$ or a protecting group for the carboxyl group.)

The compound (VII) of the present invention is produced by allowing an aldehyde compound represented by the general formula (IV) to react with a glycine compound represented by the general formula (V) and, if necessary, removing the lower alkoxy moiety of the group $R^7$ lower alkoxycarbonyl group, the amino-protecting group represented by

in the formula (V) and the carboxyl-protecting group.

This reaction is carried out by activating the compound (V) with a base such as lithium diisopropylamide, lithium bis(trimethylsilyl)amide or the like in an organic solvent such as tetrahydrofuran (THF), ether, dioxane or the like and then allowing the thus activated compound to react with the compound (IV) in an amount corresponding to the reaction at a cooling temperature to room temperature, for example, at −80° C. to room temperature. Elimination of the aralkyloxycarbonyl group in $R^{1'}$ can be effected by carrying out a commonly used hydrogen substitution reaction, for example, by adding palladium carbon or palladium chloride to the compound and stirring the mixture in a solvent such as methanol, ethanol or the like or in a mixture of a lower alcohol and an acid. Elimination of the protecting groups can be made easily in the usual way; for example, benzyl-type protecting groups can be eliminated by reduction or oxidation, acyl-type and urethane-type protecting groups by hydrolysis under an acidic or basic condition, t-butyl group by its treatment with trifluoroacetic acid or a mixture of methanol and concentrated hydrochloric acid, and methyl and ethyl groups by hydrolysis under a basic condition. According to this method, reaction of the compound (IV) with the compound (V) can be carried out at equivalent molar ratio.

Production method 2

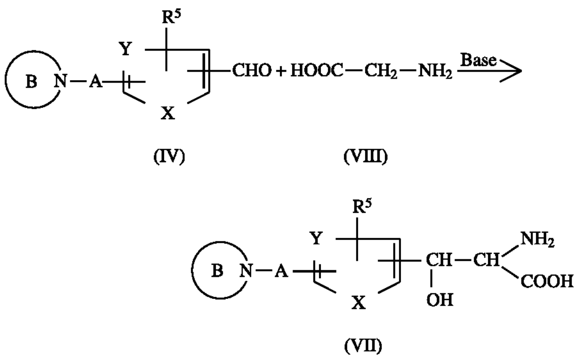

(IV) (VIII)

(VII)

(In the above formulae, X, Y, $R^5$, A and B are as defined in the foregoing.)

The compound (VII) of the present invention is produced by allowing an aldehyde compound represented by the general formula (IV) to react with free glycine (VIII).

This reaction is carried out by allowing glycine (VIII) to react with two equivalents of the compound (IV) in water, an organic solvent such as alcohols (e.g., methanol, ethanol, isopropanol or the like), or a mixture thereof in the presence of a base such as sodium hydroxide, at a cooling temperature to room temperature, for example, at 0° C. to 50° C.

Production method 3

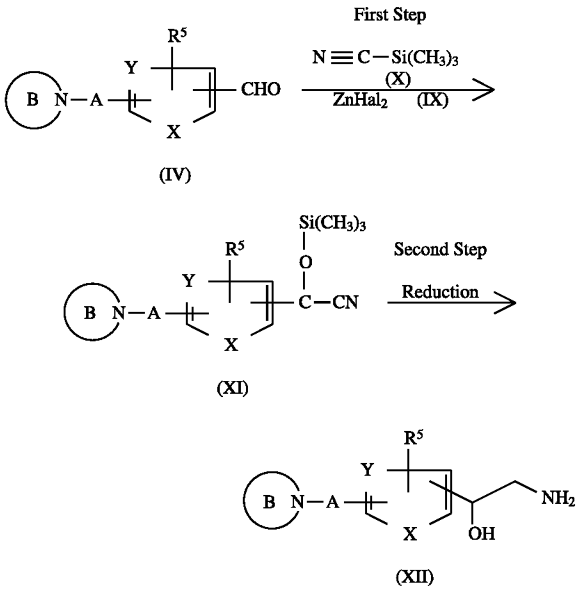

(IV)

(XI)

(XII)

(In the above formulae, X, Y, A, B and $R^5$ are as defined in the foregoing and Hal means a halogen atom, preferably, an iodine atom.)

The compound (XII) of the present invention is produced by allowing an aldehyde compound represented by the general formula (IV) to react with trimethylsilyl cyanate (X) in the presence of a zinc halide (IX) to obtain a corresponding cyanide compound (XI) (first step) and then reducing the resulting compound (second step).

This production method is effected by stirring a mixture of the aldehyde compound (IV) and trimethylsilyl cyanate (X) in an amount corresponding to the reaction in the presence of a zinc halide (IX) at room temperature or with heating to obtain the cyanide compound (XI) (first step) and then stirring the thus obtained cyanide compound (XI) in a solvent such as ether, THF, dioxane, ethylene glycol diethyl ether or the like in the presence of a reducing agent such as lithium aluminum hydride, diborane, aluminum hydride, triisobutyl aluminum or the like at cooling temperature to room temperature (second step).

Production method 4

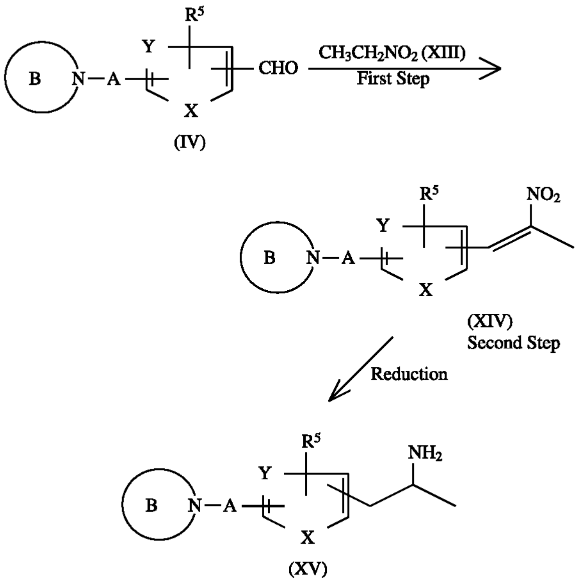

(IV)

(XIV)

(XV)

(In the above formulae, X, Y, A, B and $R^5$ are as defined in the foregoing.)

The compound (XV) of the present invention is produced by allowing an aldehyde compound represented by the general formula (IV) to react with nitroethane (XIII) to obtain a nitropropene compound (XIV) (first step) and then reducing the nitropropene compound (XIV) (second step).

This production method is effected by stirring a mixture of the aldehyde compound (IV) and nitroethane (XIII) in an amount corresponding to the reaction in a solvent such as acetic acid in the presence of ammonium acetate at room temperature or with heating to obtain the nitropropene compound (XIV) (first step) and then subjecting the thus obtained nitropropene compound (XIV) to reduction reaction in the usual way, for example, by stirring the compound in a solvent such as tetrahydrofuran, benzene, dioxane, ether or the like in the presence of a reducing agent such as lithium aluminum hydride or the like at room temperature or with heating (second step).

As an alternative method of the first step, the compound (IV) is allowed to react with the compound (XIII) in a solvent such as methanol, ethanol or the like in the presence of a catalyst such as sodium hydroxide or the like and then subjected to dehydration reaction with an acid such as hydrochloric acid, phthalic anhydride or the like.

As an alternative method of the second step, the compound (XV) can be obtained by subjecting the compound (XIV) to hydrogenation using Raney nickel in acetic acid.

Production method 5 (reduction reaction)

A compound of the present invention in which $R^1$ is a lower alkyl group can be produced by reducing a corresponding compound whose $R^1$ is an acyl group or an aralkyloxycarbonyl group. Also, a compound whose $R^3$ is a lower alkyl group substituted with a hydroxyl group can be produced by reducing a corresponding carboxyl-substituted lower alkyl compound.

This reduction reaction is carried out in a solvent such as diethyl ether, THF or the like in the presence of a reducing agent such as lithium aluminum hydride, diisobutyl aluminum hydride, diborane or the like at cooling temperature to heating temperature, for example, at 60° to 70° C. or under reflux.

Production method 6 (acylation reaction)

A compound of the present invention in which $R^1$ is an acyl group or an aralkyloxycarbonyl group can be produced by subjecting an amine compound whose $R^1$ is a hydrogen atom to acylation reaction.

This acylation reaction can be effected in the usual way, for example, by stirring a mixture of the compound whose $R^1$ is a hydrogen atom and an acylation agent (a free acid, a halide, an acid anhydride or the like) or an aralkyloxycarbonylation agent (a free acid, a halide, an acid anhydride or the like) in an inert solvent such as methylene chloride, chloroform, toluene, dioxane, ether or the like or in a heterogeneous solvent system of toluene and an aqueous alkali solution, at room temperature or with heating.

Production method 7

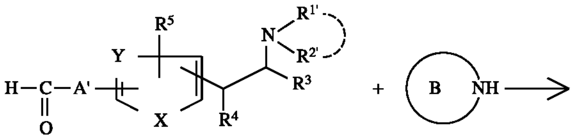

(XVI) (XVII)

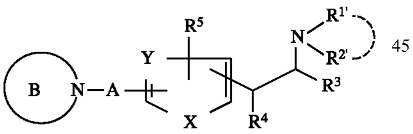

(XVIII)

(In the above formulae, X, Y, B, $R^{1'}$, $R^{2'}$, $R^2$, $R^4$ and $R^5$ are as defined in the foregoing, and A' represents a bond or a lower alkylene group smaller than A by one carbon atom.)

This reaction is effected by allowing the compound (XVI) to react with the amine (XVII) at 0° C. to 80° C. in an organic solvent such as methylene chloride, 1,2-dichloroethane, methanol, acetic acid or the like in the presence of a reducing agent such as sodium triacetoxyborohydride, sodium cyanoborohydride, sodium borohydride, a borane-pyridine complex or the like, and if necessary, adding an equivalent or excess amount of an acid. If necessary, protecting groups of the thus obtained compound of the present invention can be eliminated in the usual way similar to the case of the production method 1.

Production method 8

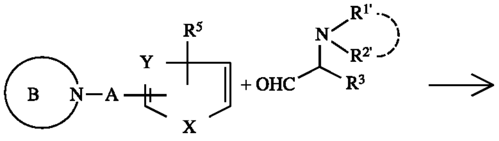

(XIX) (XX)

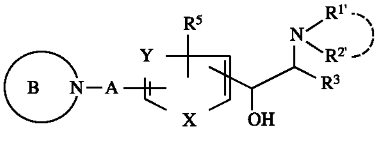

(XVIII)

(In the above formulae, X, Y, A, B, $R^{1'}$, $R^{2'}$, $R^3$ and $R^5$ are as defined in the foregoing.)

This reaction is effected by activating the compound (XIX) with a base such as organic lithium compounds (n-butyllithium, lithium diisopropylamide or the like) in an organic solvent such as tetrahydrofuran, dioxane, ether, hexane or the like, and allowing the thus activated compound to react with the compound (XX) in an amount corresponding to the reaction at cooling temperature to room temperature, for example, at −100° C. to room temperature. If necessary, protecting groups of the thus obtained compound of the present invention may be removed in the usual way similar to the case of the production method 1.

In addition, the compounds obtained by the production methods 7 and 8 can be converted into new compounds in accordance with the production method 5.

Production method 9

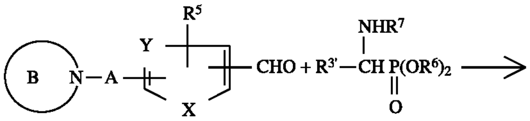

(IV) (XXI)

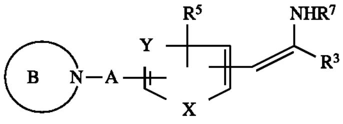

(XXII)

(In the above formulae, X, Y, A, B, $R^1$ and $R^5$ are as defined in the foregoing, $R^{3'}$ is a lower alkoxycarbonyl group as a member of $R^3$ and $R^6$ represents the aforementioned lower alkyl group.)

The compound (XXII) of the present invention is produced by allowing an aldehyde compound represented by the general formula (IV) to react with a β-ketophosphonate compound (XXI).

This reaction is effected by activating the compound (XXI) with a base such as sodium hydride, potassium hydride or the like in an organic solvent such as tetrahydrofuran, dioxane, ether or the like, and allowing the thus activated compound to react with the compound (IV) in an amount corresponding to the reaction at 0° C. to room temperature or with heating in some cases.

Production method 10

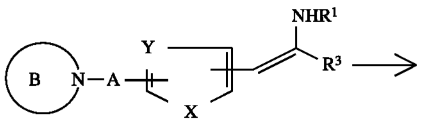

(XXII)

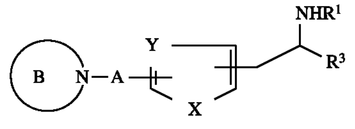

(XXIII)

(In the above formulae, X, Y, A, B, $R^1$ and $R^3$ are as defined in the foregoing.)

The compound (XXIII) of the present invention is produced by hydrogenation of the compound (XXII) at 0° C. to 100° C. in an organic solvent such as methanol, ethanol or the like using a metal catalyst such as palladium black, palladium carbon, platinum, Raney nickel or the like.

If necessary, the protecting groups may be removed in the usual way similar to the case of the production method 1.

Production method 11

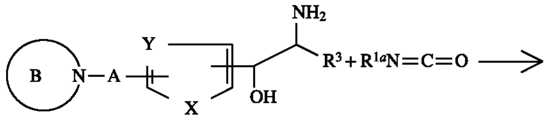

(XXIV) (XXV)

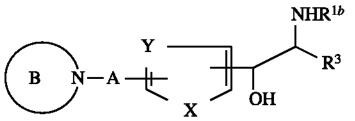

(XXVI)

(In the above formulae, $R^{1a}$ is the aforementioned aralkyl group, $R^{1b}$ is an aralkylaminocarbonyl group as a member of $R^1$, and X, Y, A, B and $R^3$ are as defined in the foregoing.)

The compound (XXVI) of the present invention is produced by allowing a serine derivative (amino compound) represented by the general formula (XXIV) to react with an isocyanate compound (XXV).

This reaction is effected by adding the isocyanate compound (XXV) in an amount corresponding to the reaction to the serine derivative (XXIV) in an organic solvent such as tetrahydrofuran, dioxane, toluene, methanol, ethanol or the like at 0° C. to room temperature or with heating if necessary. Protecting groups of the thus obtained compound of the present invention may be eliminated in the usual way similar to the case of the production method 1.

Production method 12 (alkylation)

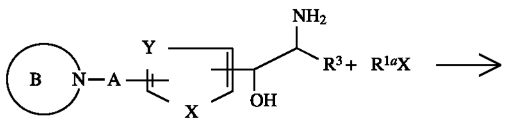

(XXIV) (XXVII)

-continued

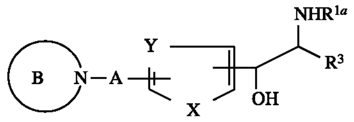

(XXVI)

(In the above formulae, X, Y, A, B, $R^{1a}$ and $R^3$ are as defined in the foregoing.)

The compound (XXIX) of the present invention is produced by allowing an amino compound represented by the general formula (XXVII) to react with an aralkyl halide or alkyl halide (XXVIII).

This reaction is effected by activating the compound XXIV with a base such as potassium carbonate, sodium carbonate, sodium hydride or the like in an organic solvent such as methanol, ethanol, isopropyl alcohol, tetrahydrofuran or the like, and allowing the thus activated compound to react with the compound XXVII in an amount corresponding to the reaction at 0° C. to room temperature or under reflux in some cases. The compounds of the present invention produced in this manner are isolated and purified in the free forms or as salts thereof.

The compounds of the present invention produced by these methods are isolated and purified in the free forms or as salts thereof. They are isolated as free compounds when treated with a small amount of an acid in the final step of the process of the present invention, and they can be isolated as salts when treated with a large quantity of an acid. Their isolation and purification are carried out by employing commonly used chemical procedures such as extraction, evaporation, crystallization, filtration, recrystallization and various types of chromatography.

The thus obtained free compounds or salts thereof can be converted into other salts by subjecting them to conventional salt forming reactions.

As described in the foregoing, the compound of the present invention contains two asymmetric carbon atoms in some cases so that optical isomers can exist.

Resolution of these isomers can be made in the usual way, for example, by fractional crystallization in which appropriate salts are recrystallized or by column chromatography. That is, they are resolved as diastereomers (R,R) form and (S,S) form or (R,S) form and (S,R) form. Diastereomers are present as enantiomers and can be resolved into two to obtain a single optical isomer, generally by the separation using a column for optical resolution or by recrystallization with appropriate salts.

INDUSTRIAL APPLICABILITY

The compound of the present invention shows a specific anti-PCP action and is useful as a psychotropic drug, an antischizophrenic drug, an antidementic drug for Alzheimer disease and the like, a drug for improving problematic behavior such as delirium caused by dementia and a drug for treating juvenile mental retardation and autism.

Anti-PCP action of the compound of the present invention has been confirmed by the following test method.

Anti-PCP action test

Test method

A compound to be tested and PCP (3 mg/kg) were administered to each male Wistar rat (body weight, 200 to 300 g) (n=8) by subcutaneous injection, and the rat was put in a hole-board apparatus (HBA) 30 minutes thereafter. HBA is an open field of 40 cm in both width and length made of a bed having 16 holes of 4 cm in diameter with walls of 20 cm in height around it [*Psychopharmacology*, 52, 271 (1977)].

Locomotion (the number of times moved through 9 divided plots on the bed) and dipping (the number of times dipped the head into holes) of each rat in the HBA were measured for 5 minutes. Male rats of Wistar line (n=8) to which PCP (3 mg/kg) was administered by subcutaneous injection were used as a control group.

In this pharmacological test, the compound of the present invention antagonized the PCP-induced increase in locomotion and decrease in dipping with a statistical significance ($p<0.01$), thus showing its strong anti-PCP action.

Test results against increase in locomotion

Example 13-(3) 3 mg/kg.sc

Example 14 3 mg/kg.sc

Test results against decrease in dipping

Example 14 3 mg/kg.sc

In addition, the compound of the present invention did not inhibit spontaneous behavior (locomotion and dipping) of rats with a dose effective in showing anti-PCP action.

On the contrary, haloperidol, which is a typical dopamine receptor blocking agent broadly used as a neuroleptic drug, also antagonized the PCP-induced locomotion, but inhibited spontaneous behavior of rats with the same dose.

A pharmaceutical preparation which contains one or more of the compounds of the present invention or salts thereof as the active ingredient is administered orally or parenterally, by making it into various dosage forms such as tablets, buccals, powders, fine granules, granules, capsules, pills, oral solutions (including syrups), injections, inhalations, suppositories, transdermal solutions, ointments, transdermal plasters, transmucosal plasters (e.g., intraoral use plasters), transmucosal solutions (e.g., transnasal solutions) and the like, making use of commonly used pharmaceutical carriers, excipients and other additives.

Solid or liquid non-toxic pharmaceutical materials are used as the carriers and excipients in the pharmaceutical preparation. Illustrative examples of such materials include lactose, magnesium stearate, starch, talc, gelatin, agar, pectin, acacia, olive oil, sesame oil, cacao butter, ethylene glycol and other commonly used materials.

Clinical dose of the compound of the present invention is optionally decided taking into consideration the disease, body weight, age and sex of each patient to be treated, as well as the route of administration and the like, and is generally from 0.1 to 1,000 mg, preferably from 1 to 200 mg, per day per adult in the case of oral administration or is generally from 0.1 to 100 mg, preferably from 0.3 to 30 mg, per day per adult in the case of intravenous injection, and the daily dose recited above may be used once a day or divided into 2 to 4 doses per day.

BEST MODE OF CARRYING OUT THE INVENTION

Examples of the present invention are given below by way of illustration and not by way of limitation.

EXAMPLE 1

(1) In a stream of argon and at −78° C., 205 ml of butyllithium (1.6 M/L, in hexane) was added dropwise to tetrahydrofuran solution (500 ml) of 32.9 g diisopropylamine and, after 10 minutes of stirring, tetrahydrofuran solution (50 ml) of 44 g t-butyl N-benzyloxycarbonylglycine ester was added thereto dropwise. After 1 hour of stirring, tetrahydrofuran solution (25 ml) of 13 g of 5-(1-pyrrolidinyl)methylthiophene-2-carboxyaldehyde was added thereto dropwise, followed by 2 hours of stirring.

After extraction with toluene-water, the organic layer was washed with a saturated sodium chloride aqueous solution and dried over anhydrous sodium sulfate, and the solvent was evaporated under reduced pressure. Then, the resulting residue was subjected to silica gel column chromatography and elution was carried out with chloroform:toluene (3:1), chloroform, and chloroform:methanol. (80:1) in that order to obtain 15.5 g (A form) and 5.2 g (B form) of two diastereomers of t-butyl 2-benzyloxycarbonylamino-3-hydroxy-3-[5-(1-pyrrolidinyl)methyl-2-thienyl]propionate.

In the following examples, a diastereomer first eluted by the silica gel column chromatography is called A form, and the secondly eluted diastereomer is called B form. In this connection, a compound formed by a reaction using a diastereomer A form (or B form) as a material is also called A form (or B form).

(2) In a stream of argon, 1.0 g of palladium carbon and 300 mg of palladium chloride were added to methanol:acetic acid:formic acid (2:2:1) mixed solution (100 ml) of 3.5 g of t-butyl 2-benzyloxycarbonylamino- 3-hydroxy-3-[5-(1-pyrrolidinyl)methyl-2-thienyl]propionate to carry out hydrogenation under stirring. After the reaction, the catalyst was removed by filtration, the solvent was evaporated under reduced pressure. Then, the residue was subjected to silica gel column chromatography and elution was carried out with chloroform:methanol (30:1) and chloroform:methanol:concentrated liquid ammonia (300:30:1) in that order to obtain 2.1 g of t-butyl 2-amino-3-hydroxy-3-[5-(1-pyrrolidinyl) methyl]-2-thienylpropionate.

(3) Methanol:concentrated hydrochloric acid (5:1) mixed solution (60 ml) was added to 2.5 g of t-butyl 2-amino-3-hydroxy-3-[5-(1-pyrrolidinyl)methyl]-2-thienylpropionate, the resulting mixture was allowed to stand for 3 hours and then the solvent was evaporated under reduced pressure. The residue was dissolved in 10 ml of ethanol and mixed with ethyl acetate and then the thus formed precipitate was immediately collected by filtration to obtain 1.7 g of 2-amino-3-hydroxy-3-[5-(1-pyrrolidinyl)methyl-2-thienyl] propionic acid.

The following compounds of Examples 2 to 4 were obtained in the same manner as shown in Example 1.

EXAMPLE 2

(1) t-Butyl 2-benzyloxycarbonylamino-3-hydroxy-3-[4-methyl-5-(1-pyrrolidinylmethyl)-2-thienyl]propionate (A form or B form)

Starting compound: 4-methyl-5-(1-pyrrolidinyl) methylthiophene-2-carboxyaldehyde (2) t-Butyl 2-amino-3-hydroxy-3-[4-methyl-5-(1-pyrrolidinyl)methyl-2-thienyl]propionate (A form)

Starting compound: t-butyl 2-benzyloxycarbonylamino-3-hydroxy-3-[4-methyl-5-(1-pyrrolidinyl)methyl-2-thienyl] propionate (A form)

(3) 2-Amino-3-hydroxy-3-[4-methyl-5-(1-pyrrolidinyl) methyl-2-thienyl]propionic acid (A form)

Starting compound: t-butyl 2-amino-3-hydroxy-3-[4-methyl-5-(1-pyrrolidinyl)methyl-2-thienyl]propionate (A form)

EXAMPLE 3

(1) t-Butyl 2-benzyloxycarbonylamino-3-hydroxy-3-[3-methyl-5-(1-pyrrolidinyl)methyl)-2-thienyl]propionate Starting compound: 3-methyl-[5-(1-pyrrolidinyl)methyl] thiophene-2-carboxyaldehyde (2) t-Butyl 2-amino-3-hydroxy-3-[3-methyl-5-(1-pyrrolidinyl)methyl-2-thienyl]propionate Starting compound: t-butyl 2-benzyloxycarbonylamino-3-hydroxy-3-[3-methyl-5-(1-pyrrolidinyl)methyl)-2-thienyl]propionate (3) 2-Amino-3-hydroxy-3-[3-methyl-5-(1-pyrrolidinyl) methyl-2-thienyl]propionic acid Starting compound: t-butyl 2-amino-3-hydroxy-3-[3-methyl-5-(1-pyrrolidinyl)methyl-2-thienyl]propionate

EXAMPLE 4

(1) Ethyl 2-benzyloxycarbonylamino-3-hydroxy-3-[5-(1-pyrrolidinyl)methyl-2-thienyl]propionate Starting compound: 5-(l-pyrrolidinyl)methylthiophene-2-carboxyaldehyde, N-benzyloxycarbonylglycine ethyl ester (2) Ethyl 2-amino-3-hydroxy-3-[5-(1-pyrrolidinyl)methyl-2-thienyl]propionate Starting compound: ethyl 2-benzyloxycarbonylamino-3-hydroxy-3-[5-(1-pyrrolidinyl)methyl-2-thienyl] propionate

EXAMPLE 5

To 2 g of 5-(1-pyrrolidinyl)methylthiophene-2-carboxyaldehyde were added 1.58 g of trimethylsilyl cyanate and 10 mg of zinc iodide in that order, followed by 2 hours of stirring at 86° C. This reaction solution was carefully added dropwise to diethyl ether suspension (200 ml) of lithium aluminum hydride, and the mixture was stirred for 1 hour. After carefully adding diethyl ether:methanol (4:1) mixed solution (50 ml), 1N sodium hydroxide aqueous solution (15 ml) and 10 g of anhydrous magnesium sulfate were added in that order, and the resulting mixture was stirred overnight. After removing the precipitate by filtration, the resulting filtrate was evaporated under reduced pressure. The residue was subjected to silica gel column chromatography and elution was carried out with chloroform:methanol (20:1), chloroform:methanol (10:1) and chloroform:methanol:concentrated aqueous ammonia (100:10:1) in that order to obtain 1.3 g of 2-amino-1-[5-(1-pyrrolidinyl)methyl-2-thienyl]ethanol.

EXAMPLE 6

(1) 5-(1-Pyrrolidinyl)methylthiophene-2-carboxyaldehyde (1 g) dissolved in 1 g of nitroethane was mixed with 400 mg of ammonium acetate and 8 ml of acetic acid, the thus prepared mixture was stirred at 125° C. for 3 hours, alkalinized with 1N sodium hydroxide aqueous solution and extracted with ether. The resulting organic layer was washed with a saturated sodium chloride aqueous solution, dried over anhydrous magnesium sulfate and evaporated under reduced pressure. Then, the thus obtained residue was subjected to silica gel column chromatography and elution was carried out with chloroform:methanol (30:1) to obtain 600 mg of 2-nitro-1-[5-(1-pyrrolidinyl)methyl-2-thienyl] propene (yellow, oily).

Physicochemical Properties

MS (m/z): GC-MS m/e 252 ($M^+$, 85%) 135 (base peak) $^1$H-NMR (400 MHz, $CDCl_3$, TMS internal standard); δ: 1.80–1.84 (4H, m), 2.54 (3H, s), 2.57–2.61 (4H, m), 3.86 (2H, s), 7.35 (1H, d), 7.37 (1H, d), 8.25 (1H, s)

(2) 2-Nitro-1-[5-(1-pyrrolidinyl)methyl-2-thienyl] propene (600 mg) dissolved in tetrahydrofuran (3 ml) was added dropwise to a tetrahydrofuran suspension of 300 mg lithium aluminum hydride at room temperature, and the mixture was stirred at 65° C. for 2 hours. After adding sodium sulfate decahydrate powder and continuing the stirring for a while, the precipitate was removed by filtration and the thus obtained filtrate was evaporated under reduced pressure. The resulting residue was mixed with 1 ml of concentrated hydrochloric acid:methanol (1:9) mixed solution and again evaporated under reduced pressure to obtain 300 mg of 1-[5-(1-pyrrolidinyl)methyl-2-thienyl]-2-propylamine dihydrochloride as viscous material.

EXAMPLE 7

To 20 ml of chloroform solution of 150 mg of 1-[5-(1-pyrrolidinyl)methyl-2-thienyl]-2-propylamine hydrochloride were added 0.2 ml of triethylamine and then 300 μl of acetic anhydride in that order. This was mixed with 1N sodium hydroxide aqueous solution (3 ml) and extracted with toluene, and the resulting organic layer was washed with a saturated sodium chloride aqueous solution and dried over anhydrous sodium sulfate. After evaporating the solvent under reduced pressure, the resulting residue was subjected to silica gel column chromatography and elution was carried out with chloroform:methanol (20:1) mixed solution to obtain 110 mg of N-1-[5-(1-pyrrolidinyl)methyl-2-thienyl]-2-propylacetamide.

EXAMPLE 8

A tetrahydrofuran solution (10 ml) of 1.2 g of t-butyl 2-benzyloxycarbonylamino-3-hydroxy-3-[5-(1-pyrrolidinyl)methyl-2-thienyl]propionate (A form) was added dropwise to 500 mg of lithium aluminum hydride in tetrahydrofuran:ether (1:1) mixed solution (50 ml) in an ice bath, and the resulting mixture was stirred for 2 hours under reflux at 50° C. Excess lithium aluminum hydride was decomposed with ether:methanol (4:1) mixed solution, and the resulting solution was mixed with 1N sodium hydroxide aqueous solution (2.5 ml) and the mixture was stirred overnight. After removing the insoluble materials by filtration, the resulting filtrate was evaporated under reduced pressure, and the thus obtained residue was subjected to silica gel column chromatography and elution was carried out with chloroform:methanol (20:1) and (10:1) and chloroform:methanol:concentrated aqueous ammonia (200:20:1) and (100:10:1) in that order to obtain 410 mg of 2-methylamino-1-[5-(1-pyrrolidinyl)methyl-2-thienyl] propane-1,3-diol (A form).

The following compounds of Examples 9 to 11 were obtained in the same manner as shown in Example 8.

EXAMPLE 9

2-Methylamino-1-[4-methyl-5-(1-pyrrolidinyl)methyl-2-thienyl]propane-1,3-diol (A form)

Starting compound: t-butyl 2-benzyloxycarbonylamino-1-[4-methyl-5-(1-pyrrolidinyl)methyl-2-thienyl]propionate

EXAMPLE 10

2-Methylamino-1-[3-methyl-5-(1-pyrrolidinyl)methyl-2-thienyl]propane-1,3-diol (A form)

Starting compound: t-butyl 2-benzyloxycarbonylamino-3-hydroxy-3-[3-methyl-5-(1-pyrrolidinyl)methyl-2-thienyl] propionate (A form)

EXAMPLE 11

2-Amino-1-[5-(1-pyrrolidinyl)methyl-2-thienyl]propane-1,3-diol (A form)

Starting compound: t-butyl 2-amino-3-hydroxy-3-[5-(1-pyrrolidinyl)methyl-2-thienyl]propionate (A form)

EXAMPLE 12

To methylene chloride solution (5 ml) of 180 mg ethyl 2-amino-3-hydroxy-3-[5-(1-pyrrolidinyl)methyl-2-thienyl] propionate diastereomers (A form and B form) was added triethylamine (300 μl), followed by dropwise addition of 80 mg of benzoyl chloride. After 30 minutes, a saturated sodium chloride aqueous solution was added to effect separation of layers, the thus separated organic layer was dried over anhydrous sodium sulfate and evaporated under reduced pressure. Then, the residue was subjected to silica gel column chromatography and elution was carried out with chloroform:methanol (30:1) mixed solution to obtain 110 mg of ethyl 2-benzoylamino-3-hydroxy-3-[5-(1-pyrrolidinyl)methyl-2-thienyl]propionate (diastereomer A form and B form).

The following compounds of Examples 13 to 20 were obtained in the same manner as the procedure of Example 1.

EXAMPLE 13

(1) t-Butyl 2-benzyloxycarbonylamino-3-[5-(1-hexahydroazepinyl)methyl-2-thienyl]propionate Starting compound: 5-(1-hexahydroazepinyl) methylthiophene-2-carboxyaldehyde (2) t-Butyl 2-amino-3-hydroxy-3-[5-(1-hexahydroazepinyl) methyl-2-thienyl]propionate Starting compound: t-butyl 2-benzyloxycarbonylamino-3-hydroxy-3-[5-(1-hexahydroazepinyl)methyl-2-thienyl] propionate (3) 2-Amino-3-hydroxy-3-[5-(1-hexahydroazepinyl) methyl-2-thienyl]propionic acid (2.0 g; yield, 63.6%)

Starting compound: t-butyl 2-amino-3-hydroxy-3-[5-(1-hexahydroazepinyl)methyl-2-thienyl]propionate (3.0 g)

EXAMPLE 14

Ethyl 2-benzyloxycarbonylamino-3-hydroxy-3-[5-(1-hexahydroazepinyl)methyl-2-thienyl]propionate (16.4 g; yield, 70.9%)

Starting compound: 5-(1-hexahydroazepinyl) methylthiophene-2-carboxyaldehyde (11.2 g)

EXAMPLE 15

Ethyl 2-benzyloxycarbonylamino-3-hydroxy-3-[5-(1-hexahydroazepinyl)methyl-2-furyl]propionate Starting compound: 5-(1-hexahydroazepinyl)methylfuran-2-carboxyaldehyde

EXAMPLE 16

Ethyl 2-benzyloxycarbonylamino-3-hydroxy-3-[2-(1-hexahydroazepinyl)methyl-5-thiazolyl]propionate Starting compound: 2-(1-hexahydroazepinyl) methylthiazole-5-carboxyaldehyde

EXAMPLE 17

Ethyl 2-benzyloxycarbonylamino-3-hydroxy-3-[5-(3-(1-hexahydroazepinyl)propyl)-2-thienyl]propionate (880 mg; yield, 50.2%)

Starting compound: 5-[3-(1-hexahydroazepinyl)propyl] thiophene-2-carboxyaldehyde (900 mg)

EXAMPLE 18

Ethyl 2-benzyloxycarbonylamino-3-hydroxy-3-[5-(1-1,2,3,6-tetrahydropyridinylmethyl)-2-thienyl]propionate Starting compound: 5-(1-1,2,3,6-tetrahydropyridinylmethyl)thiophene-2-carboxyaldehyde

EXAMPLE 19

Ethyl 2-acetylamino-3-hydroxy-3-[5-(1-pyrrolidinylmethyl)-2-thienyl]propionate

Starting compound: 5-(1-pyrrolidinyl)methylthiophene-2-carboxyaldehyde, N-acetylglycine ethyl ester

EXAMPLE 20

Ethyl 3-hydroxy-2-(1-piperidinyl-3-[5-(1-pyrrolidinylmethyl-2-thienyl]propionate Starting compound: 5-(1-pyrrolidinylmethyl)thiophene-2-carboxyaldehyde, ethyl 1-piperidineacetate The following compounds of Examples 21 to 25 were obtained by the same procedure as shown in Example 8.

EXAMPLE 21

2-Methylamino-1-[5-(1-hexahydroazepinyl)methyl-2-thienyl]propane-1-3-diol

Starting compound: t-butyl 2-benzyloxycarbonylamino-3-hydroxy-3-[5-(1-hexahydroazepinyl)methyl-2-thienyl] propionate

EXAMPLE 22

2-Methylamino-1-[5-(1-hexahydroazepinyl)methyl-2-furyl]propane-1,3-diol

Starting compound: ethyl 2-benzyloxycarbonylamino-3-hydroxy-3-[5-(1-hexahydroazepinyl)methyl-2-furyl] propionate

EXAMPLE 23

2-(1-Piperidino)-1-[5-(1-pyrrolidinylmethyl)-2-thienyl]-1,3-propanediol

Starting compound: ethyl 3-hydroxy-2-(1-piperidinyl)-3-[5-(1-pyrrolidinylmethyl)-2-thienyl]propionate

EXAMPLE 24

(+−)-2-Methylamino-1-[5-(1-pyrrolidinylmethyl)-2-thienyl]-1-propanol

Starting compound: (+−)-benzyl N-[2-hydroxy-1-methyl-2-[5-(1-pyrrolidinylmethyl)-2-thienyl]ethyl]carbamate

EXAMPLE 25

(+−)-2-Methylamino-3-phenyl-1-[5-(1-pyrrolidinylmethyl)-2-thienyl]-1-propanol

Starting compound: (+−)-benzyl N-[1-benzyl-2-hydroxy-2-[5-(1-pyrrolidinylmethyl)-2-thienyl]ethyl]carbamate The following compound of Example 26 was obtained in the same manner as shown in Example 7.

EXAMPLE 26

N-[2-Hydroxy-1-methyl-2-[5-(1-pyrrolidinylmethyl)-2-thienyl]ethyl]acetamide

Starting compound: (+−)-2-amino-[5-(1-pyrrolidinylmethyl)-2-thienyl]-1-propanol

EXAMPLE 27

To methanol solution (2 ml) of 700 mg of 5-(2-acetylamino-1-propyl)thiophene-2-carboxyaldehyde were added 0.3 ml of indoline, 1 ml of acetic acid and 1.25 g of sodium triacetoxyborohydride in that order, followed by overnight standing. This was extracted by adding chloroform and 1N sodium hydroxide, the extract was dried over anhydrous sodium sulfate and evaporated under reduced pressure. Then, the residue was subjected to silica gel column chromatography and elution was carried out with chloroform:methanol 60:1 mixed solution to obtain 350 mg of N-[2-[5-(1-indolinylmethyl)-2-thienyl]-1-methylethyl]-acetamide.

The following compounds of Examples 28 to 34 were obtained in the same manner as described in Example 27.

EXAMPLE 28

N-[1-Methyl-2-[5-[(1,2,3,6-tetrahydro-1-pyridyl)methyl] -2-thienyl]ethyl]benzamide Starting compound: 5-(2-benzoylamino-1-propyl) thiophene-2-carboxyaldehyde

EXAMPLE 29

N-[2-[5-[(4-Benzyl-1-piperidinyl)methyl]-2-thienyl]-1-methylethyl]benzamide

Starting compound: 5-(2-benzoylamino-1-propyl) thiophene-2-carboxyaldehyde

EXAMPLE 30

N-[1-Methyl-2-[5-[[4-(3-phenylpropyl)-1-piperidinyl] methyl]-2-thienyl]ethyl]benzamide Starting compound: 5-(2-benzoylamino-1-propyl) thiophene-2-carboxyaldehyde

EXAMPLE 31

N-[1-Methyl-2-[5-(1-pyrrolidinylmethyl)-2-thienyl] ethyl]benzamide

Starting compound: 5-(2-benzoylamino-1-propyl) thiophene-2-carboxyaldehyde

EXAMPLE 32

2-(2-Dimethylamino-1-propyl)-5-(1-pyrrolidinylmethyl) thiophene

Starting compound: 5-(2-dimethylamino-1-propyl) thiophene-2-carboxyaldehyde

EXAMPLE 33

N-Ethyl N-[1-methyl-2-[5-(1-hexahydroazepinylmethyl-2-thienyl]ethyl]N-phenethylamine Starting compound: 5-[2-(N-ethyl-N-phenethylamino)-1-propyl]thiophene-2-carboxyaldehyde

EXAMPLE 34

N-Ethyl N-[1-methyl-2-[5-(l-hexahydroazepinylmethyl)-2-thienyl]ethyl]N-(3-phenyl)-1-propylamine Starting compound: 5-[2-[N-ethyl-N-(3-phenyl)-1-propyl] amino-1-propyl]thiophene-2-carboxyaldehyde

EXAMPLE 35

(1) In a stream of argon and at −78° C., 51 ml of hexane solution containing 1.6 mol of n-butyllithium was added dropwise to 200 ml of tetrahydrofuran solution containing 13.45 g of 2-(1-pyrrodinylmethyl)thiophene, and the mixture was stirred for 30 minutes. After dropwise addition of 10 ml of tetrahydrofuran solution containing 5.56 g of 2-benzyloxycarbonylaminopropylaldehyde and subsequent 1 hour of stirring, this was mixed with ammonium chloride aqueous solution and extracted with toluene. The resulting organic layer was dried over anhydrous sodium sulfate and evaporated under reduced pressure. Then, the residue was subjected to silica gel column chromatography and elution was carried out with a series of chloroform:methanol mixtures of 50:1, 40:1, 30:1 and 20:1 in that order to obtain 3.6 g of the compound of interest.

(2) (+−)-Benzyl N-[2-hydroxy-1-methyl-2-[5(1-pyrrolidinylmethyl)-2-thienyl]ethyl]carbamate (2.5 g) was dissolved in 100 ml of acetic acid and 20 ml of formic acid and 400 mg of palladium chloride and 600 mg of 10% palladium carbon were added thereto in a stream of argon to effect hydrogenation, followed by overnight stirring. After filtration, the filtrate was evaporated under reduced pressure. The resulting residue was subjected to silica gel column chromatography and elution was carried out with chloroform:methanol=30:1, 20:1 and 10:1 and chloroform-:methanol:concentrated aqueous ammonia=200:20:1 and 100:10:1 in that order to obtain 948 mg of the compound of interest.

The following compounds of Examples 36 to 38 were obtained in the same manner as described in Example 35.

EXAMPLE 36

(1) (+−)-Benzyl N-[1-benzyl-2-hydroxy-2-[5-(1-pyrrolidinylmethyl)-2-thienyl]ethyl]carbamate Starting compound: 2-benzyloxycarbonylamino-3-phenylpropylaldehyde, 2-(1-pyrrolidinylmethyl) thiophene (2) (+−)-2-Amino-3-phenyl-l-[5-(1-pyrrolidinylmethyl)-2-thienyl]-1-propanol Starting compound: (+−)-benzyl N-[1-benzyl-2-hydroxy-2-[5-(1-pyrrolidinylmethyl)-2-thienyl]ethyl]carbamate

EXAMPLE 37

2-Benzyloxycarbonylamino-1-[5-(1-hexahydroazepinyl) methyl-2-thienyl]propanol

Starting compound: 2-(1-hexahydroazepinyl) methylthiophene

EXAMPLE 38

2-Amino-3-phenyl-1-[5-(1-hexahydroazepinyl)methyl-2-thienyl]-1-propanol

Starting compound: 2-(1-hexahydroazepinyl) methylthiophene

EXAMPLE 39

In a stream of argon, 1.1 g of 60% sodium hydride was washed with hexane and mixed with 50 ml of tetrahydrofuran. Then, 10 ml of 8.3 g tetrahydrofuran solution was added thereto dropwise at 0° C. After completion of hydrogen gas generation, 10 ml of tetrahydrofuran solution containing 5.6 g of 5-(1-hexahydroazepinyl)methylthiophene-2-carboxyaldehyde was added thereto, followed by 2 hours of stirring. This was extracted with ether, the resulting extract was dried by adding anhydrous sodium sulfate and evaporated under reduced pressure. Then, the residue was subjected to silica gel column chromatography and elution was carried out with a mixed solution of chloroform:methanol=60:1 to obtain 6.4 g of methyl 2-benzyloxycarbonylamino-3-[5-(1-hexahydroazepinylmethyl)-2-thienyl]propenoate.

EXAMPLE 40

In an atmosphere of argon, 30 ml of methanol solution containing 2.03 g of the compound of Example 39 was mixed with 500 mg of palladium black and stirred for 3 days to effect hydrogenation. Then, 1 g of activated carbon was added and the mixture was filtered. The filtrate was evaporated under reduced pressure and then the residue was subjected to silica gel column chromatography and elution was carried out with a series of mixed solutions of chloroform:methanol=40:1 and 20:1 and chloroform:methanol:concentrated aqueous ammonia=300:10:1 and 100:10:1 in that order to obtain 120 mg of methyl 2-benzyloxycarbonylamino-3-[5-(1-hexahydroazepinylmethyl)-2-thienyl]propionate.

EXAMPLE 41

2-Benzyloxycarbonylamino-1-[5-(1-hexahydroazepinylmethyl)-2-thienyl]-1-butanol was obtained in the same manner as described in Example 35 (1).

Starting compound: 2-(1-hexahydroazepinyl) methylthiophene, 2-benzyloxycarbonylaminobutynal

EXAMPLE 42

2-Amino-1-[5-(1-hexahydroazepinylmethyl)-2-thienyl]-1-butanol was obtained in the same manner as described in Example 35 (2).

Starting compound: 2-benzyloxycarbonylamino-1-[5-(1-hexahydroazepinylmethyl)-2-thienyl]-1-butanol

EXAMPLE 43

3-Phenylpropyl bromide (352 mg) and 250 mg of potassium carbonate were added to 25 ml of ethanol solution containing 500 mg of 2-amino-1-[5-(1-hexahydroazepinylmethyl)-2-thienyl]-1-butanol, and the mixture was stirred for 24 hours. After evaporation under reduced pressure, the residue was subjected to silica gel column chromatography and elution was carried out with mixed solutions of chloroform:methanol=20:1 and 10:1 and chloroform:methanol:concentrated aqueous ammonia=100:10:1 in that order to obtain 250 mg of 1-[5-(1-hexahydroazepinylmethyl)-2-thienyl]-2-(3-phenyl) propylamino-1-butanol.

The following compounds of Examples 44, 46 and 49 were obtained in the same manner as described in Example 1.

EXAMPLE 44

(1) ±Erythroethyl 3-[5-(1-hexahydroazepinylmethyl)-2-thienyl]-3-hydroxy-2-piperidinopropionate Starting compound: 5-(1-hexahydroazepinyl) methylthiophene-2-carboxyaldehyde, ethyl piperidinoacetate (2) ±Threoethyl 3-[5-(1-hexahydroazepinylmethyl)-2-thienyl]-3-hydroxy-2-piperidinopropionate Starting compound: 5-(1-hexahydroazepinyl) methylthiophene-2-carboxyaldehyde, ethyl piperidinoacetate

EXAMPLE 45

(1) ±Threo 1-[5-(1-hexahydroazepinylmethyl)-2-thienyl]-3-hydroxy-2-piperidino-1,3-propanediol was obtained in the same manner as described in Example 8 (1).

Starting compound: ethyl 3-[5-(1-hexahydroazepinylmethyl)-2-thienyl]-2-piperidinopropionate (2) (±)Erythroethyl 3-[5-(1-hexahydroazepinylmethyl)-2-thienyl]-3-hydroxy-2-piperidino-1,3-propanediol was obtained in the same manner as described in Example 8 (2).

Starting compound: ethyl 3-[5-(1-hexahydroazepinylmethyl)-2-thienyl]-3-hydroxy-2-piperidinopropionate

EXAMPLE 46

(1) (±)-Erythroethyl 2-tert-butoxycarbonylamino-3-[5-(1-hexahydroazepinylmethyl)-2-thienyl]-3-hydroxypropionate Starting compound: 5-(1-hexahydroazepinyl) methylthiophene-2-carboxyaldehyde, ethyl N-tert-butoxycarbonylaminoacetate (2) (±)-Threoethyl 2-tert-butoxycarbonylamino-3-[5-(1-hexahydroazepinylmethyl)-2-thienyl]-3-hydroxypropionate

EXAMPLE 47

Ethyl 3-hydroxy-3-[5-(1-hexahydroazepinylmethyl)-2-thienyl]propionate was obtained in the same manner as described in Example 13.

Starting compound: ethyl 2-amino-3-hydroxy-3-[5-(1-hexahydroazepinylmethyl)-2-thienyl]propionate

EXAMPLE 48

2-(1,3-Dihydroxy-2-methylamino)propyl-5-(2-1,2,3,4-tetrahydroisoquinolyl)methylthiophene.4/3 L-tartrate (diastereomer mixture) was obtained in the same manner as described in Example 8.

Starting compound: ethyl 2-benzyloxycarbonylamino-3-hydroxy-3-[5-(2-1,2,3,4-tetrahydroisoquinolylmethyl)-2-thienyl]propionate

EXAMPLE 49

Ethyl 3-hydroxy-2-(3-phenyl)propylamino-3-[5-(1-hexahydroazepinylmethyl)-2-thienyl]propionate.2HCl Starting compound: ethyl 3-phenylpropylaminoacetate, 5-(1-hexahydroazepinyl)methylthiophene-2-carboxyaldehyde

EXAMPLE 50

Benzyl isocyanate (300 mg, 2.3 mmol) is added dropwise to tetrahydrofuran solution of ethyl 2-amino-3-hydroxy-3-[5-(1-hexahydroazepinyl)methyl-2-thienyl]propionate (800 mg, 2.5 mmol).

After a whole day and night of reflux of this solution, the reaction is terminated with a saturated sodium chloride aqueous solution, followed by ethyl acetate extraction. The organic layer is dried over anhydrous sodium sulfate and the solvent is evaporated. By purifying the resulting residue by silica gel column chromatography ($CHCl_3$:MeOH=80:1→50:1), ethyl 2-benzylaminocarbonylamino-3-hydroxy-3-[5-(1-hexahydroazepinyl)methyl-2-thienyl] propionate was obtained (450 mg, 1.0 mmol, 43%).

EXAMPLE 51

A mixed solution of concentrated hydrochloric acid:ethanol=1:5 (60 ml) was added to 12.6 g of ethyl 2-tert-butoxycarbonylamino-3-hydroxy-3-[5-(1-hexahydroazepinylmethyl)-2-thienyl]propionate, and the mixture was immediately concentrated under reduced pressure, mixed with 60 ml of the above mixed solution and again concentrated under reduced pressure. The resulting residue was subjected to silica gel column chromatography and elution was carried out with mixed solutions of chloroform:ethanol=60:1, chloroform:methanol=20:1 and 10:1 and chloroform:methanol:concentrated aqueous ammonia=100:10:1 in that order to obtain 8.9 g of ethyl 2-amino-3-hydroxy-3-[5-(1-hexahydroazepinylmethyl)-2-thienyl]propionate.

TABLE 4

<table>
<tr><th>Ex. No.</th><th>Structural Formula</th><th>Physicochemical Properties</th></tr>
<tr><td>1-(1)</td><td>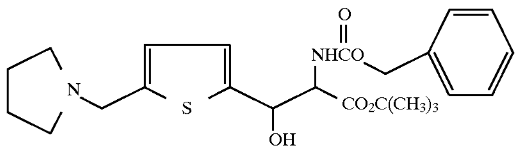</td><td>MS(m/z): FAB Pos. 461(M$^+$ + 1, 30%)<br>91 (base peak)<br>$^1$H-NMR(400MHz. $CDCl_3$, TMS Int. St.)<br>δ: 1.44(9H, s), 1.75~1.78(4H, m),<br>2.53(4H, brm), 3.74(2H, s),<br>4.52(1H, brd), 5.10(2H, s),<br>5.33(1H, brs), 5.61(1H, brd),<br>6.75(1H, d), 6.84(1H, d),<br>7.30~7.36(5H, m)/A form<br><br>MS(m/z): FAB Pos. 461(M$^+$ + 1, 20%)<br>91 (base peak)<br>$^1$H-NMR(400MHz, $CDCl_3$, TMS Int. St.)<br>δ: 1.41(9H, s), 1.75~1.79(4H, m),<br>2.53(4H, brm), 3.75(2H, s),<br>4.71(1H, brm), 5.14(2H, s),<br>5.38(1H, brm), 5.63(1H, br),<br>6.74(2H, s), 7.31~7.37(5H, m)/B form</td></tr>
<tr><td>1-(2)</td><td>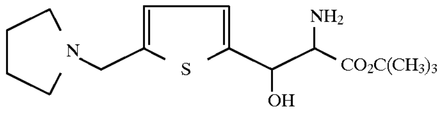</td><td>MS(m/z): FAB Pos. 327(M$^+$ + 1, base peak)<br>$^1$H-NMR(400MHz, $CD_3OD$, TMS Int. St.)<br>δ: 1.42(9H, s), 1.88~1.91(4H, m),<br>2.82~2.86(4H, m), 3.68(1H, d),<br>4.06(2H, s), 5.11(1H, d), 6.92(1H, d),<br>6.78(1H, d)/A form<br><br>MS(m/z): FAB Pos. 327(M$^+$ + 1, 85%) 127(base peak)<br>$^1$H-NMR(400MHz, $CDCl_3$, TMS Int. St.)<br>δ: 1.41(9H, s), 1.80(4H, quint),<br>1.90~2.60(3H, br), 2.60(4H, brm),<br>3.60(1H, d), 3.81(2H, s), 4.98(1H, d),<br>6.80(1H, d), 6.83(1H, d)/B form</td></tr>
<tr><td>1-(3)</td><td>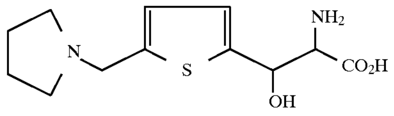</td><td>Hygroscopic<br>Anal. (for $C_{12}H_{18}N_2O_3S.2HCl.H_2O$)
<table>
<tr><th></th><th>C (%)</th><th>H (%)</th><th>N (%)</th><th>S (%)</th><th>Cl (%)</th></tr>
<tr><td>Calcd.</td><td>39.89</td><td>6.14</td><td>7.75</td><td>8.88</td><td>19.63</td></tr>
<tr><td>Measured</td><td>40.02</td><td>6.58</td><td>7.56</td><td>8.83</td><td>19.24</td></tr>
</table>
MS(m/z): FAB (Pos. 271(M$^+$ + 1, 10%)<br>93 (base peak)<br>$^1$H-NMR(400MHz, $D_2O$, TMS Int. St.)<br>δ: 1.96~2.01(2H, m), 2.12~2.19(2H, m),<br>3.16~3.23(2H, m), 3.53~3.58(2H, m),<br>4.35(1H, d), 4.58(2H, s), 5.65(1H, d),<br>7.10(1H, d), 7.25(1H, d)/A form<br><br>Anal. (for $C_{12}H_{18}N_2O_3S.2HCl.1.5H_2O$)
<table>
<tr><th></th><th>C (%)</th><th>H (%)</th><th>N (%)</th><th>S (%)</th><th>Cl (%)</th></tr>
<tr><td>Calcd.</td><td>38.92</td><td>6.26</td><td>7.57</td><td>8.66</td><td>19.15</td></tr>
<tr><td>Measured</td><td>39.04</td><td>6.51</td><td>7.30</td><td>8.68</td><td>18.94</td></tr>
</table>
MS(m/z): FAB Pos. 271(M$^+$ + 1, 30%)<br>93 (base peak)<br>$^1$H-NMR(400MHz, $D_2O$, TMS Int. St.)<br>δ: 1.98~2.03(2H, m), 2.14~2.19(2H, m),<br>3.18~3.25(2H, m), 3.53~3.59(2H, m),<br>4.28(1H, d), 4.59(2H, s), 5.61(1H, d),<br>7.14(1H, d), 7.26(1H, d)/B form</td></tr>
</table>

TABLE 5

| Ex. No. | Structural Formula | Physicochemical Properties |
|---|---|---|
| 2 (1) | 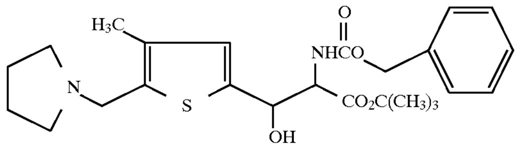 | MS(m/z): FAB Pos. 475($M^+$ + 1, 55%)<br>91 (base peak)<br>$^1$H-NMR(500MHz, $CDCl_3$, TMS Int. St.)<br>δ: 1.41(9H, s), 1.74~1.77(4H, m),<br>2.11(3H, s), 2.52~2.55(4H, m),<br>3.66(1H, d), 3.69(1H, d),<br>3.94(1H, br), 4.69(1H, m),<br>5.14(2H, s), 5.32(1H, brd), 5.61(1H, brd),<br>6.61(1H, s), 7.32~7.37(5H, m)/A form |
| | | MS(m/z): FAB Pos. 475($M^+$ + 1, 30%)<br>91 (base peak)<br>$^1$H-NMR(500MHz, $CDCl_3$, TMS Int. St.)<br>δ: 1.44(9H, s), 1.74~1.78(4H, m),<br>2.11(3H, s), 2.52~2.56(4H, m),<br>3.10~3.30(1H, br), 3.67(2H, s),<br>4.50(1H, brd), 5.10(2H, s),<br>5.28(1H, s), 5.62(1H, brd),<br>6.70(1H, s), 7.31~7.34(5H, m)/B form |
| 2-(2) | 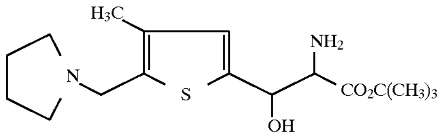 | MS(m/z): FAB Pos. 341($M^+$ + 1, 90%)<br>141 (base peak)<br>$^1$H-NMR(400MHz, $CDCl_3$, TMS Int. St.)<br>δ: 1.42(9H, s), 1.78~1.82(4H, m),<br>2.14(3H, s), 2.60~2.64(4H, m),<br>3.71(1H, brd), 3.75(2H, s),<br>5.06(1H, d), 6.67(1H, s)/A form |
| 2-(3) | 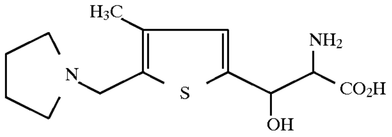 | MS(m/z): FAB Pos. 285($M^+$ + 1, base peak)<br>$^1$H-NMR(400MHz, $D_2O$, TMS Int. St.)<br>δ: 1.96~2.04(2H, m), 2.11~2.19(2H, m),<br>2.25(3H, s), 3.16~3.24(2H, m),<br>3.54~3.62(2H, m), 4.12(1H, d),<br>4.52(2H, s), 5.56(1H, d), 6.95(1H, s)/A form |

TABLE 6

| Ex. No. | Structural Formula | Physicochemical Properties |
|---|---|---|
| 3-(1) | 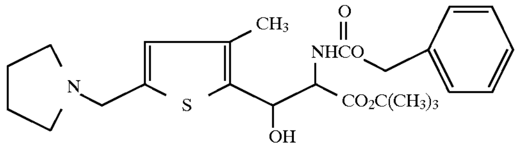 | MS(m/z): FAB Pos. 475($M^+$ + 1, 85%)<br>91 (base peak)<br>$^1$H-NMR(400MHz, $CDCl_3$, TMS Int. St.)<br>δ: 1.36(9H, s), 1.75~1.78(4H, m),<br>2.17(3H, s), 2.50~2.54(4H, m),<br>3.69(1H, d), 3.70(1H, d),<br>4.66(1H, brm), 5.14(2H, s),<br>5.42(1H, brd), 5.70(1H, brd),<br>6.60(1H, s), 7.31~7.38(5H, m)/A form |
| | | MS(m/z): FAB Pos. 475($M^+$ + 1, 65%)<br>91 (base peak)<br>$^1$H-NMR(400MHz, $CDCl_3$, TMS Int. St.)<br>δ: 1.44(9H, s), 1.65(1H, br),<br>1.75~1.78(4H, m), 2.17(3H, s),<br>2.50~2.54(4H, m), 3.69(2H, s),<br>4.43(1H, brd), 5.08(2H, s),<br>5.41(1H, brd), 5.61(1H, brd),<br>6.61(1H, s), 7.32~7.38(5H, m)/B form |
| 3-(2) | | MS(m/z): FAB Pos. 341($M^+$ + 1, 95%)<br>141 (base peak)<br>$^1$H-NMR(400MHz, $CDCl_3$, TMS Int. St.) |

TABLE 6-continued

| Ex. No. | Structural Formula | Physicochemical Properties |
|---|---|---|
| | 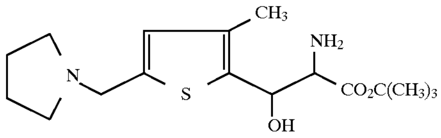 | δ: 1.37(9H, s), 1.76~1.80(4H, m),<br>1.60~2.20(3H, br), 2.20(3H, s),<br>2.51~2.59, (4H, m), 3.73(2H, s),<br>3.74(1H, d), 5.14(1H, d),<br>6.61(1H, s)/A form |
| | | MS(m/z): FAB Pos. 341($M^+$ + 1, 95%)<br>140 (base peak)<br>$^1$H-NMR(400MHz, $CDCl_3$, TMS Int. St.)<br>δ: 1.36(9H, s), 1.60~2.20(3H, br),<br>1.76~1.80(4H, m), 2.15(3H, s),<br>2.51~2.59(4H, m), 3.51(1H, d),<br>3.73(2H, s), 4.96(1H, d),<br>6.61(1H, s)/B form |
| 3-(3) | 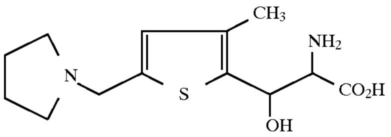 | MS(m/z): FAB Pos. 285($M^+$ + 1, base peak)<br>$^1$H-NMR(400MHz, $D_2O$, TMS Int. St.)<br>δ: 1.94~2.01(2H, m), 2.11~2.19(2H, m),<br>2.25(3H, s), 3.17~3.24(2H, m),<br>3.51~3.59(2H, m), 4.20(1H, d),<br>4.52(2H, s), 5.61(1H, d), 7.08(1H, s)/A form |
| | | MS(m/z): FAB Pos. 285($M^+$ + 1, base peak)<br>$^1$H-NMR(400MHz, $D_2O$, TMS Int. St.)<br>δ: 1.94~2.01(2H, m),<br>2.11~2.19(2H, m), 2.25(3H, s),<br>3.17~3.24(2H, m), 3.51~3.59(2H, m),<br>4.06(1H, d), 4.52(1H, s),<br>5.53(1H, d), 7.08(1H, s)/B form |

TABLE 7

| Ex. No. | Structural Formula | Physicochemical Properties |
|---|---|---|
| 4-(1) | 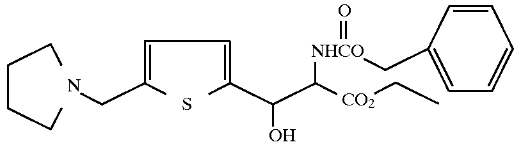 | MS(m/z): FAB Pos. 433($M^+$ + 1, 15%)<br>91 (base peak)<br>$^1$H-NMR(400MHz, $CDCl_3$, TMS Int. St.)<br>δ: 1.24(3H, t), 1.77(4H, quint),<br>2.52(4H, brt), 3.75(2H, s),<br>4.18(2H, q), 4.81(1H, dd), 5.14(2H, s),<br>5.40(1H, brd), 5.60(1H, brd),<br>6.73(1H, d), 6.74(1H, d),<br>7.31~7.39(5H, m)/A form |
| | | MS(m/z): FAB Pos. m/e 433($M^+$ + 1, 35%)<br>91 (base peak)<br>$^1$H-NMR(400MHz, $CDCl_3$, TMS Int. St.)<br>δ: 1.26(3H, t), 1.76(4H, quint),<br>2.52(4H, brs), 3.73(2H, s),<br>4.22(2H, q), 4.61(1H, dd), 5.10(2H, s),<br>5.40(1H, brs), 5.69(1H, d), 6.74(1H, d),<br>6.83(1H, d), 7.31~7.35(5H, m)/B form |
| 4-(2) | 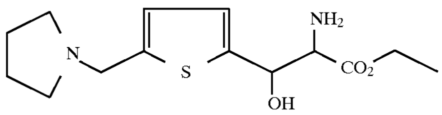 | Liquid<br>MS(m/z): FAB Pos. 299($M^+$ + 1, base peak)<br>$^1$H-NMR(400MHz, $CD_3OD$, TMS Int. St.)<br>δ: 1.27(3H, t), 2.12(4H, br), 3.24(2H, br),<br>3.56(2H, br), 4.30(2H, dq), 4.42(1H, d),<br>4.60(2H, s), 5.54(1H, d), 7.06(1H, d),<br>7.30(1H, d)/A form |
| | | MS(m/z): FAB Pos. 299($M^+$ + 1. base peak)<br>$^1$H-NMR(400MHz, $CD_3OD$, TMS Int. St.)<br>δ: 1.29(3H, t), 2.12(4H, br),<br>3.24(2H, br), 3.56(2H, br),<br>4.30(2H, dq), 4.35(1H, d), 4.62(2H, s),<br>5.50(1H, d), 7.13(1H, d), 7.31(1H, d)/B form |
| 5 | | Anal. (for $C_{11}H_{18}N_2OS.1.5C_4H_6O_6.1.5H_2O$) |

TABLE 7-continued

| Ex. No. | Structural Formula | Physicochemical Properties |
|---|---|---|
| | 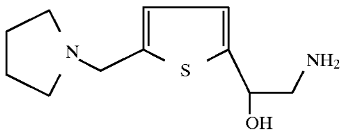 | C (%) H (%) N (%) S (%)<br>Calcd. 42.67 6.32 5.85 6.70<br>Measured 42.96 6.32 6.04 6.88<br>MS(m/z): FAB Pos. 227($M^+$ + 1, 80%)<br>127 (base peak)<br>$^1$H-NMR(400MHz, DMSO-$d_6$, TMS Int. St.)<br>δ: 1.64~1.72(4H, m), 2.39~2.46(4H, m), 2.64(1H, dd), 2.68(1H, dd), 3.31(2H, br), 3.68(2H, s), 4.57(1H, dd), 5.50(1H, br), 6.73(1H, d), 6.75(1H, d) |

TABLE 8

| Ex. No. | Structural Formula | Physicochemical Properties |
|---|---|---|
| 6 | 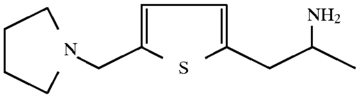<br>.2HCl | MS(m/z): FAB Pos. Matrix MBA m/e 255 ($M^+$ + 1, base peak)<br>$^1$H-NMR(400MHz, $CD_3OD$, TMS Int. St.)<br>δ: 1.35(3H, d), 2.12(4H, brs), 3.10(1H, dd), 3.21(1H, dd), 3.37(4H, brs), 3.48~3.54(1H, m), 4.55(2H, s), 6.97(1H, d), 7.24(1H, d) |
| 7 | 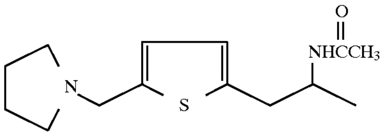 | MS(m/z): FAB Pos. Matrix MBA m/e 267 ($M^+$ + 1, base peak)<br>$^1$H-NMR(400MHz, $CDCl_3$, TMS Int. St.)<br>δ: 1.14(3H, d), 1.78~1.82(4H, m), 1.96(3H, s), 2.56~2.59(4H, m), 2.91(1H, dd), 2.97(1H, dd), 3.77(2H, s), 4.21~4.28(1H, m), 5.41(1H, brd), 6.63(1H, d), 6.76(1H, d) |
| 8 | 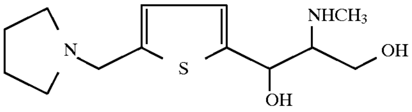 | MS(m/z): FAB Pos. 271($M^+$ + 1, 80%)<br>74 (base peak)<br>$^1$H-NMR(400MHz, $CD_3OD$, TMS Int. St.)<br>δ: 1.79~1.82(4H, m), 2.38(3H, s), 2.57~2.60(4H, m), 2.69(1H, dd), 3.65(1H, dd), 3.68(1H, dd), 3.80(2H, s), 4.97(1H, d), 6.86(1H, d), 6.87(1H, d) A form |

TABLE 9

| Ex. No. | Structural Formula | Physicochemical Properties |
|---|---|---|
| 9 | 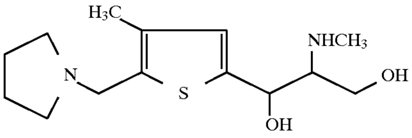 | MS(m/z): FAB Pos. 285($M^+$ + 1, 25%)<br>74 (base peak)<br>$^1$H-NMR(400MHz, $CD_3OD$, TMS Int. St.)<br>δ: 2.05~2.09(4H, m), 2.29(3H, s), 2.83(3H, s), 3.33~3.37(4H, m), 3.39~3.43(1H, m), 3.73(1H, dd), 3.83(1H, dd), 4.48(2H, s), 5.35(1H, brd), 6.92(1H, s) |
| 10 | | MS(m/z): FAB Pos. 285($M^+$ + 1, 45%)<br>74 (base peak)<br>$^1$H-NMR(400MHz, $CDCl_3$, TMS Int. St.) |

TABLE 9-continued

| Ex. No. | Structural Formula | Physicochemical Properties |
|---|---|---|
| | 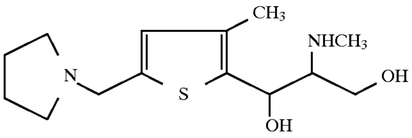 | δ: 1.77~1.79(4H, m), 2.16(3H, s), 2.44(3H, s), 2.05~2.50(3H, br), 2.55~2.57(4H, m), 2.70(1H, dd), 3.69(1H, dd), 3.73(2H, s), 3.77(1H, dd), 5.06(1H, d), 6.63(1H, s) |
| 11 | 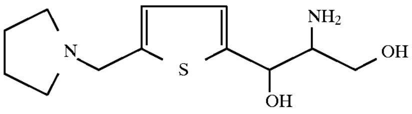 | MS(m/z): FAB Pos. 257($M^+$ + 1, 25%)<br>93 (base peak)<br>$^1$H-NMR(500MHz, $CD_3OD$, TMS Int. St., as tartrate)<br><br>δ: 2.06(4H, brm), 3.20~3.90(7H, m), 4.40(2H, s), 4.52(1H, d), 6.96~7.26(2H, m) |

TABLE 10

| Ex. No. | Structural Formula | Physicochemical Properties |
|---|---|---|
| 12 | 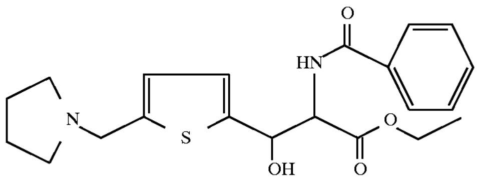 | MS(m/z): FAB Pos. 403($M^+$ + 1, 20%)<br>102 (base peak)<br>$^1$H-NMR(400MHz, $CDCl_3$, TMS Int. St.)<br><br>δ: 1.28~1.34(3H, m), 1.85(4H, br), 2.89(4H, brm), 4.07(2H, s), 4.23~4.30(2H, m), 4.80~4.86(1H, m), 5.11~5.14(1H, m), 5.60~5.62(1H, m), 6.97(1H, d), 7.01(1H, d), 7.19~8.06(5H, m) |
| 13-(1) | 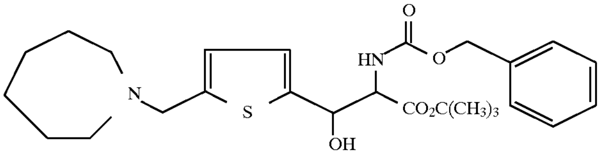 | MS(m/z): EI 488($M^+$, 2%)<br>$^1$H-NMR(400MHz, $CDCl_3$, TMS Int. St.)<br><br>δ: 1.41(9H, s), 1.43~1.59(8H, m), 2.61~2.64(4H, m), 3.77(2H, s), 4.71(1H, m), 5.14(2H, s), 5.35~5.40(1H, m), 5.64(1H, d, J=7.8Hz), 6.71(1H, d, 3.4Hz), 6.75(1H, d, J=3.4Hz), 7.32~7.37(5H, m) |
| 13-(2) | 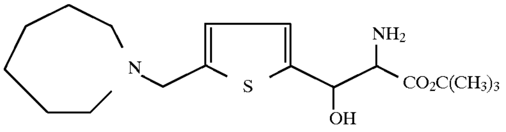 | MS(m/z): EI 354($M^+$, 0.5%)<br>$^1$H-NMR(400MHz, $CDCl_3$, TMS Int. St.)<br><br>δ: 1.41(9H, s), 1.55~1.68(8H, m), 2.30~2.55(2H, br), 2.63~2.67(4H, m), 3.73(1H, d, J=5.4Hz), 3.78(2H, s), 5.11(1H, d, J=5.4Hz,) 6.72(1H, d, J=3.4Hz), 6.79(1H, d, J=3.4Hz) |

TABLE 11

| Ex. No. | Structural Formula | Physicochemical Properties |
|---|---|---|
| 13-(3) | 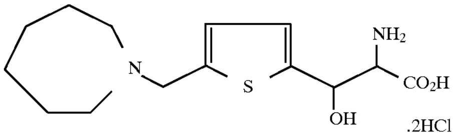 | MS(m/z): FAB Pos. 299($M^+$ + 1, base peak)<br>$^1$H-NMR(400MHz, $CD_3OD$, TMS Int. St.)<br><br>δ: 1.65~1.85(4H, m), 1.85~2.00(4H, m), 3.13~3.20(2H, m), 3.42~3.57(2H, m), 4.35(1H, d, J=3.4Hz), 4.57(2H, s), 5.59(1H, d, J=3.4Hz), 7.07(1H, d, J=3.4Hz), 7.33(1H, d, J=3.4Hz) |

TABLE 11-continued

| Ex. No. | Structural Formula | Physicochemical Properties |
|---|---|---|
| 14 | 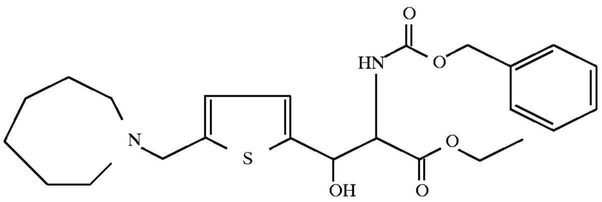 | Anal.: (for $C_{24}H_{33}N_2O_5S$)<br>C (%) H (%) N (%) S (%)<br>Calcd. 62.59 7.00 6.08 6.96<br>Measured 62.21 7.04 6.08 6.81<br>MS(m/z): EI 460($M^+$, 3%)<br>$^1$H-NMR(400MHz, $CDCl_3$, TMS Int. St.)<br>δ: 1.21~1.27(3H, m), 1.53~1.68(8H, m), 2.61~2.67(4H, m), 3.75(2H, s), 4.15~4.23(2H, m), 4.60~4.66(0.4H, m), 4.75~4.82(0.6H, m), 5.09(0.4H, s), 5.13(0.6H, s), 5.37~5.41(1H, m), 5.61~5.63(0.6H, m), 5.74~5.76(0.4H, m), 6.71~6.84(2H, m), 7.26~7.35(5H, m) |
| 15 | 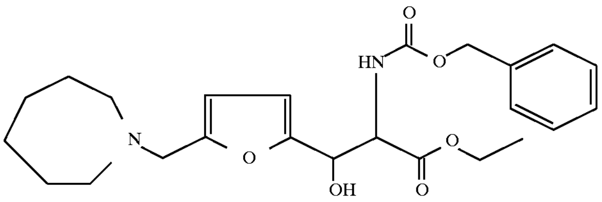 | MS(m/z): EI 444($M^+$, 7%)<br>$^1$H-NMR(400MHz, $CDCl_3$, TMS Int. St.)<br>δ: 1.18~1.27(3H, m), 1.56~1.58(8H, m), 2.58~2.61(4H, m), 3.60(2H, s), 4.08~4.21(2H, m), 4.69~4.78(1H, m), 5.07~5.23(3H, m), 5.78~5.80(1H, m), 6.07~6.08(1H, m), 6.20~6.22(1H, m), 7.27~7.34(5H, m) |

TABLE 12

| Ex. No. | Structural Formula | Physicochemical Properties |
|---|---|---|
| 16 | 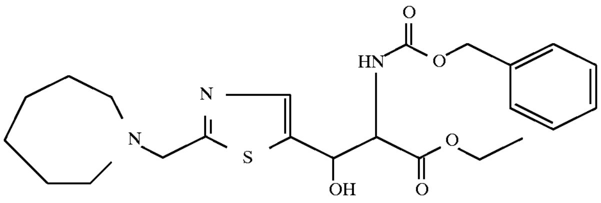 | MS(m/z): FAB Pos. 462($M^+$ + 1, base peak)<br>$^1$H-NMR(400MHz, $CDCl_3$, TMS Int. St.)<br>δ: 1.22~1.28(3H, m), 1.52~1.70(8H, m), 2.69~2.72(4H, m), 3.86(0.8H, s), 3.87(1.2H, s), 4.16~4.27(2H, m), 4.50~4.62(0.6H, m), 4.75~4.82(0.4H, m) 5.09(0.4H, d, J=4.9Hz), 5.14(0.6H, s), 5.46~5.50(1H, m), 5.72(0.6H, d, J=6.8Hz), 5.81(0.4H, d, J=9.3Hz), 7.27~7.41(5H, m), 7.44(0.6H, s), 7.53(0.4H, s) |
| 17 | 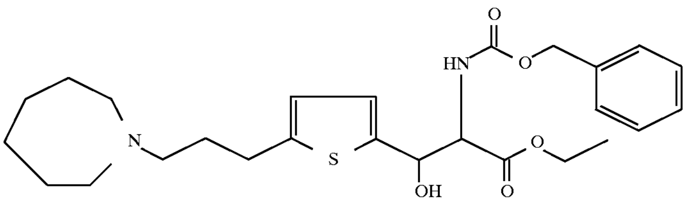 | MS(m/z): FAB Pos. 489($M^+$ + 1, 33%)<br>$^1$H-NMR(400MHz, $CDCl_3$, TMS Int. St.)<br>δ: 1.21~1.30(3H, m), 1.52~1.67(8H, m), 1.71~1.80(2H, m), 2.43~2.48(2H, m), 2.57~2.60(4H, m), 2.71~2.77(2H, m), 4.16~4.21(2H, m), 4.57~4.59(0.5H, m), 4.73~4.77(0.5H, m), 5.10(1H, s), 5.12(1H, s), 5.35~5.39(1H, m), 5.60(0.5H, d, J=7.8Hz), 5.77(0.5H, d, J=9.3Hz), 6.57~6.59(1H, m), 6.70(0.5H, d, J=3.4Hz), 6.80(0.5H, d, J=3.4Hz), 7.27~7.34(5H, m) |

TABLE 12-continued

| Ex. No. | Structural Formula | Physicochemical Properties |
|---|---|---|
| 18 | 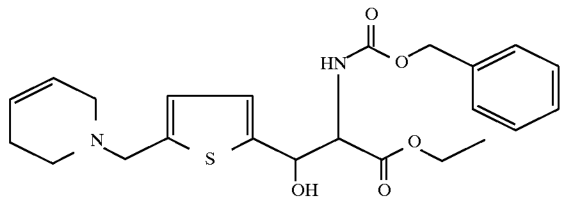 | MS(m/z): EI 444($M^+$, 10%)<br>$^1$H-NMR(400MHz, $CDCl_3$, TMS Int. St.)<br>δ: 1.21~1.27(3H, s), 2.12~2.20(2H, m), 2.56(2H, t, J=5.9Hz), 2.96~2.98(2H, m), 3.70(0.3H, s), 3.71(0.7H, s), 4.12~4.20(2H, m), 4.60~4.62(0.3H, m), 4.74~4.82(0.7H, m) 5.08(0.6H, s), 5.12(1.4H, s), 5.37~5.41(1H, m), 5.61~5.77(3H, m), 6.75~6.84(2H, m), 7.27~7.34(5H, m) |

TABLE 13

| Ex. No. | Structural Formula | Physicochemical Properties |
|---|---|---|
| 19 | 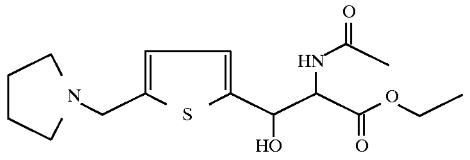 | MS(m/z): HR-MS for $C_{16}H_{25}N_2O_4S$<br>Calcd. 341.153504<br>Measured 341.153715<br>$^1$H-NMR(400MHz, $CDCl_3$, TMS Int. St.)<br>δ: 1.29(3H, t), 1.76~1.80(4H, m), 2.10(3H, s), 2.53~2.54(4H, m), 3.76(2H, s), 4.23(2H, q), 5.05(1H, dd), 5.48(1H, d), 6.39(1H, d), 6.69(1H, d), 6.76(1H, d) |
| 20 | 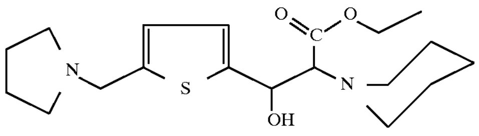 | MS(m/z): HR-MS for $C_{19}H_{31}N_2O_3S$<br>Calcd. 367.205540<br>Measured 367.207820<br>$^1$H-NMR(400MHz, $CDCl_3$, TMS Int. St.)<br>δ: 1.19(3H, t), 1.47~1.66(6H, m), 1.75~1.79(4H, m), 2.42~2.54(6H, m) 2.82~2.88(2H, m), 3.21(1H, d), 3.74(1H, d), 3.77(1H, d), 4.05~4.16(2H, m), 4.54(1H, s), 5.05(1H, d), 6.73(1H, d), 6.82(1H, d)/A form<br>$^1$H-NMR(400MHz, $CDCl_3$, TMS Int. St.)<br>δ: 1.30(3H, t), 1.39~1.67(6H, m), 1.76~1.82(4H, m), 2.41~2.47(2H, m), 2.56~2.58(4H, m), 2.67~2.73(2H, m), 3.28(1H, d), 3.79~3.83(2H, m), 4.17~4.29(2H, m), 5.17(1H, d), 6.76(1H, d), 6.90(1H, d)/B form |
| 21 | 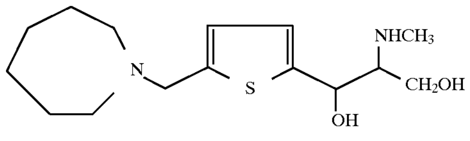 | MS(m/z): FAB Pos. 299($M^+$ + 1, 28%)<br>$^1$H-NMR(400MHz, $CDCl_3$, TMS Int. St.)<br>δ: 1.52~1.68(8H, m), 2.39(3H, s), 2.62~2.65(4H, m), 3.64~3.68(1H, m), 3.74~3.78(4H, m), 3.70~3.95(1H, br), 5.00(1H, d, J=4.4Hz), 6.73(1H, d, J=3.4Hz), 6.78(1H, d, J=3.4Hz) |

TABLE 14

| Ex. No. | Structural Formula | Physicochemical Properties |
|---|---|---|
| 22 | 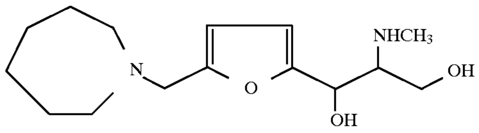 | MS(m/z): FAB Pos. 283($M^+$ + 1, 75%)<br>$^1$H-NMR(400MHz, $CDCl_3$, TMS Int. St.)<br>δ: 1.50~1.68(8H, m), 2.42(0.9H, s), 2.44(2.1H, s), 2.56~2.68(4H, m), 3.37~3.41(1H, m), 3.00~3.45(2H, br), 3.61(2H, s), 3.65~3.73(2H, m), 4.65(0.3H, d, J=7.4Hz), 4.83(0.7H, d, J=5.3Hz), 6.12~6.16(1H, m), 6.23~6.24(1H, m) |
| 23 | 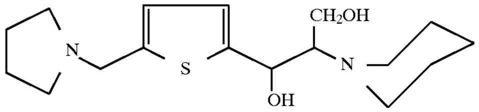 | mp: 108~109° C. (chloroform-hexane)<br>MS(m/z): HR-MS for $C_{17}H_{29}N_2O_2S$<br>Calcd. 325.194975<br>Measured 325.193358<br>$^1$H-NMR(400MHz, $CDCl_3$, TMS Int. St.)<br>δ: 1.38~1.44(2H, m), 1.46~1.55(4H, m), 1.74~1.77(4H, m), 2.53~2.56(8H, m), 2.76~2.81(1H, m), 3.68(1H, dd), 3.75(2H, s), 3.78(1H, dd), 5.03(1H, d), 6.76(1H, d), 6.81(1H, d)/A form |
| | | colorless transparent liquid<br>MS(m/z): HR-MS for $C_{17}H_{29}N_2O_2S$<br>Calcd. 325.194975<br>Measured 325.196275<br>$^1$H-NMR(400MHz, $CDCl_3$, TMS Int. St.)<br>δ: 1.48~1.57(2H, m), 1.59~1.66(4H, m), 1.73~1.80(4H, m), 2.36(1H, br), 2.53(4H, brs), 2.65~2.74(3H, m), 2.84~2.90(2H, m), 3.50(1H, dd), 3.59(1H, dd), 3.73(1H, d), 3.76(1H, d), 4.64(1H, d), 6.73(1H, d), 6.73(1H, d), 6.81(1H, d)/B form |
| 24 | 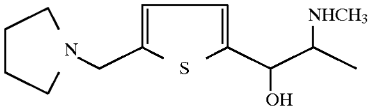 | MS(m/z): HR-MS for $C_{13}H_{23}N_2OS$<br>Calcd. 255.153110<br>Measured 255.154112<br>$^1$H-NMR(400MHz, $CDCl_3$, TMS Int. St.)<br>δ: 0.97~1.02(3H, m), 1.55~1.75(2H, br), 1.76~1.82(4H, m), 2.45(3H, s), 2.54~2.55(4H, m), 2.63~2.68(0.5H, m), 2.79~2.84(0.5H, m), 3.77(2H, s), 4.38(0.5H, d), 4.84(0.5H, d), 6.73~6.38(2H, m) |

TABLE 15

| Ex. No. | Structural Formula | Physicochemical Properties |
|---|---|---|
| 25 | 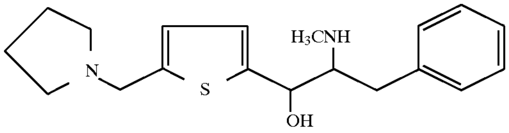 | MS(m/z): HR-MS for $C_{19}H_{27}N_2OS$<br>Calcd. 331.184411<br>Measured 331.189259<br>$^1$H-NMR(400MHz, $CD_3OD$, TMS Int. St.)<br>δ: 1.79~1.83(4H, m), 2.28(3H, d), 2.54~2.62(4H, m), 2.40~3.02(3H, m), 3.79~3.82(2H, m), 4.68~4.70(0.5H, m), 4.91~4.93(0.5H, m), 6.83~6.89(2H, m), 7.13~7.30(5H, m) |
| 26 | | MS(m/z): FAB Pos. 283($M^+$ + 1, base peak)<br>$^1$H-NMR(400MHz, $CDCl_3$, TMS Int. St.) |

TABLE 15-continued

| Ex. No. | Structural Formula | Physicochemical Properties |
|---|---|---|
| | 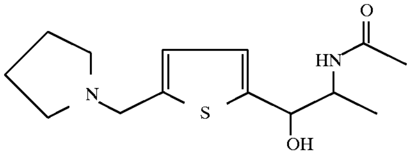 | δ: 1.09(1.5H, d), 1.20(1.5H, d), 1.82~1.87(4H, m), 1.98(1.5H, s), 2.03(1.5H, s), 2.71~2.80(4H, m), 3.91~3.94(2H, m), 4.18~4.23(0.5H, m), 4.36~4.41(0.5H, m), 4.84(0.5H, d), 4.98(0.5H, d), 6.01(1H, brd), 6.79~6.87(2H, m) |
| 27 | 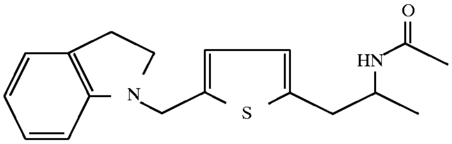 | MS(m/z): HR-MS for $C_{18}H_{22}N_2OS$<br>Calcd. 314.145285<br>Measured 314.146451<br>$^1$H-NMR(400MHz, $CDCl_3$, TMS Int. St.)<br>δ: 1.14(3H, d), 1.96(3H, s), 2.85~3.07(5H, m), 3.31~3.35(1H, m), 4.22~4.29(1H, m), 4.37(2H, s), 5.39(1H, br), 6.56~7.17(6H, m) |

TABLE 16

| Ex. No. | Structural Formula | Physicochemical Properties |
|---|---|---|
| 28 | 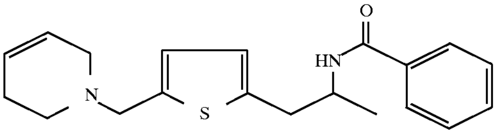 | MS(m/z): HR-MS for $C_{20}H_{25}N_2OS$<br>Calcd. 341.168760<br>Measured 341.170982<br>$^1$H-NMR(500MHz, $CDCl_3$, TMS Int. St.)<br>δ: 1.27(3H, d), 1.60(4H, brs), 2.15~2.17(2H, m), 2.57~2.60(2H, t), 3.00~3.01(2H, m), 3.02(1H, dd), 3.13(1H, dd), 3.74(2H, s), 4.44~4.48(1H, m), 5.63~5.65(1H, m), 5.73~5.75(1H, m), 6.01(1H, d), 6.70(1H, d), 6.77(1H, d), 7.42(2H, t), 7.48(1H, t), 7.71~7.73(2H, m) |
| 29 | 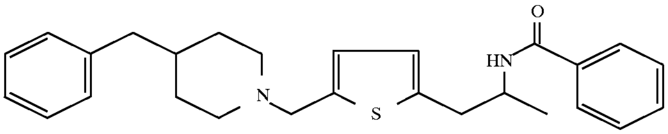 | MS(m/z): HR-MS for $C_{27}H_{33}N_2OS$<br>Calcd. 433.231361<br>Measured 433.230913<br>$^1$H-NMR(500MHz, $CDCl_3$, TMS Int. St.)<br>δ: 1.26(3H, d), 1.26~1.33(3H, m), 1.46~1.49(1H, m), 1.60(2H, brd), 1.92(2H, brt), 2.51(2H, d), 2.98~3.03(2H, m), 3.01(1H, dd), 3.63(2H, s), 4.41~4.47(1H, m), 6.02(1H, brd), 6.67(1H, d), 6.72(1H, d), 7.11~7.13(2H, d), 7.18(1H, t), 7.25~7.28(2H, m), 7.39~7.42(3H, m), 7.71~7.74(2H, m) |
| 30 | | MS(m/z): HR-MS for $C_{29}H_{37}N_2OS$<br>Calcd. 461.262661<br>Measured 461.263538<br>$^1$H-NMR(400MHz, $CDCl_3$, TMS Int. St.) |

TABLE 16-continued

| Ex. No. | Structural Formula | Physicochemical Properties |
|---|---|---|
| | 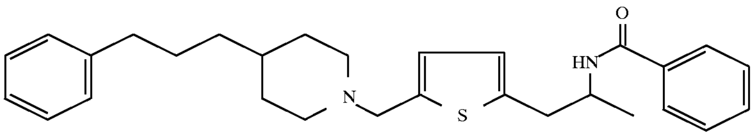 | δ: 1.20~1.28(8H, s), 1.56~1.62(4H, m), 1.93(2H, brt), 2.55~2.59(2H, t), 2.86~2.89(2H, br), 3.01(1H, dd), 3.11(1H, dd), 3.63(2H, s), 4.44~4.48(1H, m), 6.02(1H, brd), 6.68(1H, d), 6.73(1H, d), 7.15~7.18(3H, m), 7.25~7.29(2H, m), 7.36~7.42(2H, m), 7.45~7.49(1H, m), 7.71~7.73(2H, m) |

TABLE 17

| Ex. No. | Structural Formula | Physicochemical Properties |
|---|---|---|
| 31 | 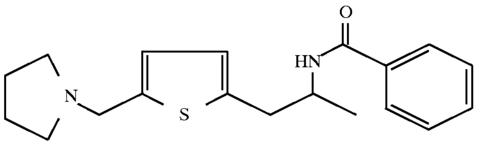 | MS(m/z): HR-MS for $C_{19}H_{25}N_2OS$<br>Calcd. 329.168760<br>Measured 329.170228<br>$^1$H-NMR(400MHz, $CDCl_3$, TMS Int. St.)<br><br>δ: 1.27(3H, d), 1.76~1.81(4H, m), 2.54~2.56(4H, m), 3.02(1H, dd), 3.13(1H, dd), 3.76(2H, s), 4.43~4.50(1H, m), 6.02(1H, brd), 6.68(1H, d), 6.77(1H, d), 7.40~7.43(2H, m), 7.48~7.51(1H, m), 7.71~7.73(2H, d) |
| 32 | 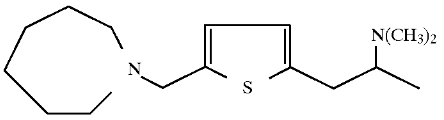 | MS(m/z): HR-MS for $C_{16}H_{29}N_2S$<br>Calcd. 281.205146<br>Measured 281.202950<br>$^1$H-NMR(400MHz, $CDCl_3$, TMS Int. St.)<br><br>δ: 0.99(3H, d), 1.61~1.64(8H, m), 2.27(6H, s), 2.59~2.67(5H, m), 2.76~2.83(1H, m), 3.02~3.06(1H, dd), 3.78(2H, s), 6.60(1H, d), 6.67(1H, d) |
| 33 | 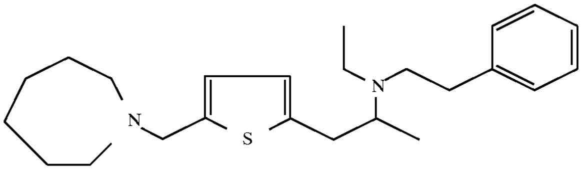 | MS(m/z): FAB Pos. 385($M^+$ + 1, base peak)<br>$^1$H-NMR(400MHz, $CD_3OD$, TMS Int. St.)<br><br>δ: 1.35~1.37(3H, m), 1.44~1.49(3H, m), 1.71~1.77(4H, m), 1.82~1.96(4H, m), 3.15~3.28(4H, m), 3.41~3.51(8H, m), 3.85~3.86(1H, m), 4.56(2H, s), 7.03~7.05(1H, m), 7.25~7.29(1H, m), 7.28~7.37(5H, m) |

TABLE 18

| Ex. No. | Structural Formula | Physicochemical Properties |
|---|---|---|
| 34 | 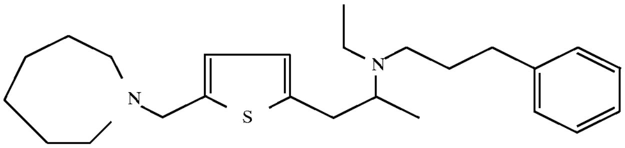 | MS(m/z): HR-MS for $C_{25}H_{39}N_2S$<br>Calcd. 399.283396<br>Measured 399.282520<br>$^1$H-NMR(400MHz, $CDCl_3$, TMS Int. St.)<br>δ: 0.97(3H, d), 1.03(3H, t), 1.59(8H, brs), 1.76(2H, quint), 2.43~2.66(7H, m), 2.94~3.03(2H, m), 3.77(2H, s), 6.58(1H, d), 6.66(1H, d), 7.14~7.18(3H, m), 7.24~7.28(2H, m) |
| 35-(1) | 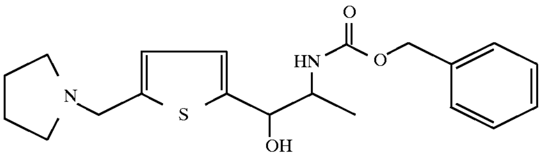 | MS(m/z): FAB Pos. 375($M^+$ + 1, 80%)<br>$^1$H-NMR(400MHz, $CDCl_3$, TMS Int. St.)<br>δ: 1.10(3H, d), 1.19(1.5H, d), 1.77~1.78(4H, brs), 1.60~1.80(1H, br) 2.54~2.55(4H, brm), 3.76(2H, s), 3.95~4.15(1H, m), 4.81~5.13(4H, m), 6.75~6.81(2H, m), 7.32~7.37(5H, m) |
| 35-(2) | 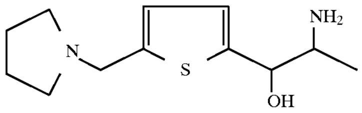 | MS(m/z): HR-MS for $C_{12}H_{21}N_2OS$<br>Calcd. 241.137460<br>Measured 241.134571<br>$^1$H-NMR(400MHz, $CDCl_3$, TMS Int. St.)<br>δ: 1.04~1.09(3H, m), 1.77~1.80(4H, m), 1.99(3H, br), 2.54~2.58(4H, m), 3.05~3.12(0.5H, m), 3.15~3.22(0.5H, m), 3.78(2H, s), 4.42(0.5H, d,), 4.66(0.5H, d,), 6.76~6.81(2H, m) |

TABLE 19

| Ex. No. | Structural Formula | Physicochemical Properties |
|---|---|---|
| 36-(1) | 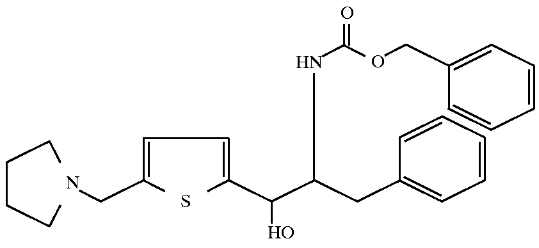 | MS(m/z): FAB Pos. 451($M^+$ + 1, 85%)<br>$^1$H-NMR(400MHz, $CDCl_3$, TMS Int. St.)<br>δ: 1.88~1.89(4H, m), 2.71~3.03(6H, m), 3.95~3.99(2H, brm), 4.04~4.24(1H, m), 4.92~5.33(4H, m), 6.81~6.88(1H, m), 6.92~7.00(1H, m), 7.14~7.35(10H, m) |
| 36-(2) | 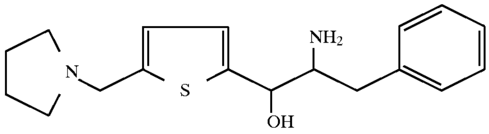 | MS(m/z): HR-MS for $C_{18}H_{25}N_2OS$<br>Calcd. 317.168760<br>Measured 317.171368<br>$^1$H-NMR(400MHz, $CDCl_3$, TMS Int. St.)<br>δ: 1.81~1.83(4H, brs), 1.50~2.30(3H, m), 2.40~2.46(0.5H, dd), 2.48~2.54(0.5H, dd), 2.61~2.64(4H, br), 2.87~2.94(1H, m), 3.20~3.33(1H, m), 3.84(1.5H, s), 3.84(1.5H, s), 4.62(0.5H, d), 4.81(0.5H, d), 6.83~6.87(2H, m), 7.18~7.33(5H, m) |

TABLE 19-continued

| Ex. No. | Structural Formula | Physicochemical Properties |
|---|---|---|
| 37 | 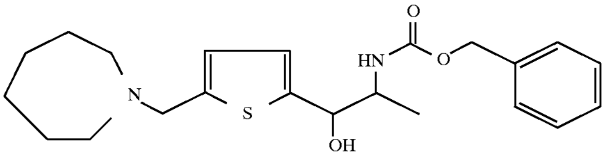 | MS(m/z): FAB Pos. 403($M^+$ + 1, 40%)<br>$^1$H-NMR(400MHz, $CDCl_3$, TMS Int. St.)<br><br>δ: 1.07(1.5H, d, J=6.6Hz),<br>1.16(1.5H, d, J=6.6Hz),<br>1.50~1.67(8H, m), 2.60~2.64(4H, m),<br>3.74(1H, s), 3.75(1H, s),<br>4.30~4.52(1H, br),<br>4.75~4.80(0.5H, m),<br>4.93~4.98(0.5H, m),<br>5.04~5.08(2H, m), 5.31~5.33(1H, m),<br>6.69~6.76(2H, m), 7.28~7.33(5H, m) |

TABLE 20

| Ex. No. | Structural Formula | Physicochemical Properties |
|---|---|---|
| 38 | 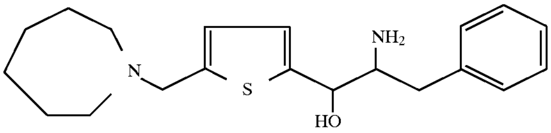 | MS(m/z): FAB Pos. 345($M^+$ + 1, 20%)<br>$^1$H-NMR(400MHz, $CDCl_3$, TMS Int. St.)<br><br>δ: 1.62~1.66(8H, m), 2.41~2.52(4H, m),<br>2.68~2.95(4H, m), 2.86~2.95(1H, m),<br>3.22~3.45(1H, m), 3.84(0.5H, s),<br>3.85(0.5H, s), 4.62(0.5H, d, J=5.3Hz),<br>4.81(0.5H, d, J=5.3Hz),<br>6.77~6.86(2H, m),<br>7.17~7.32(5H, m) |
| 39 | 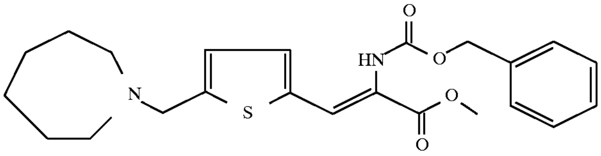 | MS(m/z): FAB m/e 4.29($M^+$ + 1, 40%)<br>91 (base peak)<br>$^1$H-NMR($CDCl_3$, 400MHz, TMS Int. St.)<br><br>δ: 1.60~1.64(8H, m), 2.65~2.68(4H, m),<br>3.78~3.89(5H, m), 5.17(2H, s),<br>6.03(1H, brs), 6.86(1H, d),<br>7.18(1H, d), 7.31~7.39(5H, m),<br>7.69(1H, s) |
| 40 | 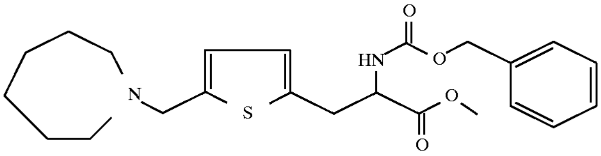 | MS(m/z): FAB m/e 431($M^+$ + 1, base peak)<br>$^1$H-NMR($CDCl_3$, 400MHz, TMS Int. St.)<br><br>δ: 1.58~1.62(8H, m), 2.61~2.68(4H, m),<br>3.30(2H, d), 3.74(3H, s), 3.85(2H, s),<br>4.63~4.65(1H, m), 5.12(2H, s),<br>5.38(1H, d), 6.88~6.94(2H, m),<br>7.30~7.37(5H, m) |

TABLE 21

| Ex. No. | Structural Formula | Physicochemical Properties |
|---|---|---|
| 41 | 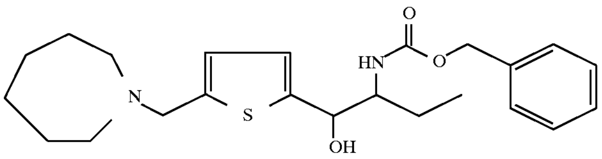 | MS(m/z): FAB m/e 417($M^+$ + 1, 45%),<br>91 (base peak)<br>$^1$H-NMR($CDCl_3$, 400MHz, TMS Int. St.)<br><br>δ: 0.95(1.5H, t), 0.96(1.5H, t),<br>1.23~1.36(0.5H, m),<br>1.44~1.52(0.5H, m),<br>1.59~1.69(9H, brs),<br>2.63~2.66(4H, t), 3.78(2H, s),<br>4.82(0.5H, d), 4.89(0.5H, d),<br>5.00(0.5H, s), 5.02(0.5H, s),<br>5.10(1H, s), 5.14(1H, s),<br>6.73(0.5H, d), 6.74(0.5H, d),<br>6.77(0.5H, d), 6.80(0.5H, d),<br>7.30~7.37(5H, m) |
| 42 | 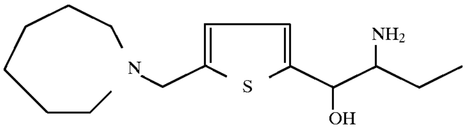 | MS(m/z): FAB m/e 283($M^+$ + 1, 65%)<br>58 (base peak)<br>$^1$H-NMR($CDCl_3$, 400MHz, TMS Int. St.)<br><br>δ: 0.93~0.99(3H, m), 1.13~1.31(1H, m),<br>1.47~1.51(1H, m), 1.50~1.63(8H, m),<br>1.70(3H, br), 2.65~2.68(4H, m),<br>2.80~2.95(1H, m), 3.81(2H, s),<br>4.51(0.5H, d), 4.75(0.5H, d),<br>6.74~6.76(1H, m), 6.79~6.81(1H, m) |
| 43 | 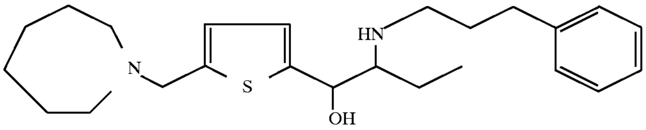 | MS(m/z): HR-MS for $C_{24}H_{37}N_2OS$<br>Calcd. 401.262661<br>Measured 401.257824<br>$^1$H-NMR($CDCl_3$, 400MHz, TMS Int. St.)<br><br>δ: 0.58~0.97(3H, dt), 1.22~1.45(2H, m),<br>1.60~1.63(8H, brm), 1.77~1.87(2H, m),<br>1.20~2.10(2H, br), 2.45~2.84(8H, m)<br>3.79(1H, s), 3.80(1H, s), 4.47(0.5H, d),<br>4.88(0.5H, d), 6.71~6.81(2H, m),<br>7.16~7.20(3H, m), 7.25~7.30(2H, m) |

TABLE 22

| Ex. No. | Structural Formula | Physicochemical Properties |
|---|---|---|
| 44-(1) | 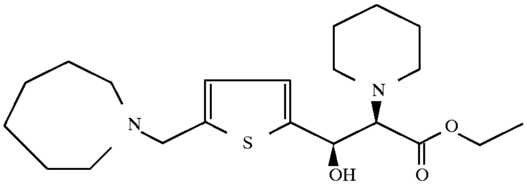 | MS(m/z): HR-MS for $C_{21}H_{35}N_2O_3S$<br>Calcd. 395.236840<br>Measured 395.233118<br>$^1$H-NMR($CDCl_3$, 400MHz, TMS Int. St.)<br><br>δ: 1.18(3H, t), 1.47~1.53(3H, m),<br>1.59~1.67(11H, m),<br>2.40~2.54(2H, m),<br>2.62~2.67(4H, m),<br>2.83~2.87(2H, m), 3.22(1H, d),<br>3.78(2H, s), 4.06~4.15(2H, m),<br>4.52(1H, s), 5.04(1H, d),<br>6.69(1H, d), 6.81(1H, d) |
| 44-(2) | 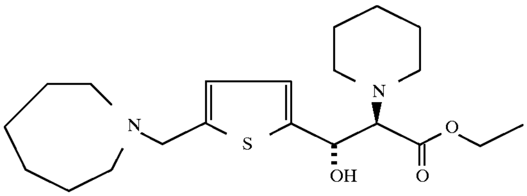 | MS(m/z): HR-MS for $C_{21}H_{35}N_2O_3S$<br>Calcd. 395.236840<br>Measured 395.233385<br>$^1$H-NMR($CDCl_3$, 400MHz, TMS Int. St.)<br><br>δ: 1.30(3H, t), 1.36~1.42(2H, m),<br>1.43~1.56(4H, m), 1.59~1.64(8H, m),<br>2.42~2.47(2H, m), 2.62~2.66(4H, m),<br>2.68~2.72(2H, m), 3.29(1H, d),<br>3.80(2H, s), 41.6~4.29(2H, m),<br>5.17(1H, d), 6.73(1H, d), 6.88(1H, d) |

TABLE 22-continued

| Ex. No. | Structural Formula | Physicochemical Properties |
|---|---|---|
| 45-(1) | 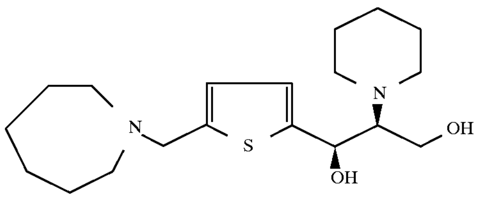 | MS(m/z): HR-MS m/l for $C_{19}H_{33}N_2O_2S$<br>Calcd. 353.226275<br>Measured 353.223412<br>$^1$H-NMR($CDCl_3$, 400MHz, TMS Int. St.)<br><br>δ: 1.49~1.61(14H, m), 2.63~2.76(7H, m), 2.85~2.90(2H, m), 3.54(1H, dd), 3.62(1H, dd), 3.79(2H, s), 4.67(1H, d), 6.72(1H, dd), 6.83(1H, d) |

TABLE 23

| Ex. No. | Structural Formula | Physicochemical Properties |
|---|---|---|
| 45-(2) | 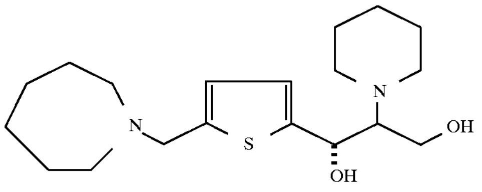 | MS(m/z): HR-MS for $C_{19}H_{33}N_2O_2S$<br>Calcd. 353.226275<br>Measured 353.222557<br>$^1$H-NMR($CDCl_3$, 400MHz, TMS Int. St.)<br><br>δ: 1.40~1.56(6H, m), 1.61(8H, brm), 2.56~2.61(4H, m), 2.63~2.67(4H, m), 2.85(1H, dd), 2.20~3.20(2H, br), 3.69(1H, dd), 3.80(2H, s), 3.81(1H, dd), 5.08(1H, d), 6.75(1H, d), 6.83(1H, d) |
| 46-(1) | 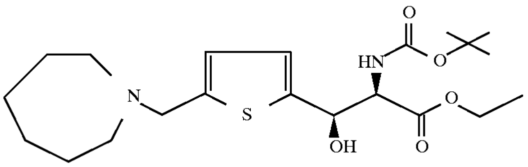 | MS(m/z): HR-MS for $C_{21}H_{35}NO_5S$<br>Calcd. 427.226669<br>Measured 427.228628<br>$^1$H-NMR($CDCl_3$, 400MHz, TMS Int. St.)<br><br>δ: 1.26(3H, t), 1.46(9H, s), 1.60(8H, brs), 2.62~2.68(4H, m), 3.78(2H, s), 4.20(2H, q), 4.75(1H, br), 5.38(2H, brs), 6.73(2H, brs) |
| 46-(2) | 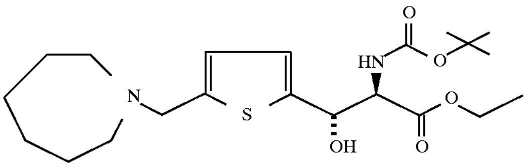 | MS(m/z): HR-MS for $C_{21}H_{35}N_2O_5S$<br>Calcd. 427.226669<br>Measured 427.230517<br>$^1$H-NMR($CDCl_3$, 400MHz, TMS Int. St.)<br><br>δ: 1.28(3H, t), 1.44(9H, brs), 1.61~1.65(8H, m), 2.68(4H, brs), 2.90~3.10(1H, br), 3.81(2H, s) 4.23(2H, q), 4.55(1H, brd), 5.39(2H, br), 6.76(1H, d), 6.87(1H, d) |

TABLE 24

| Ex. No. | Structural Formula | Physicochemical Properties |
|---|---|---|
| 47 | 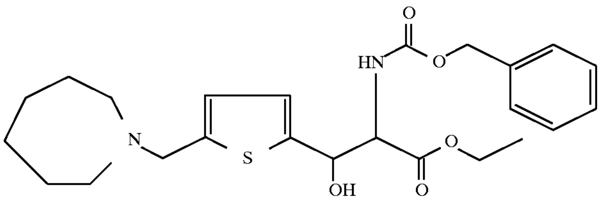 | MS(m/z): HR-MS for $C_{25}H_{35}N_2O_4S$<br>Calcd. 459.231755<br>Measured 459.234861<br>$^1$H-NMR($CDCl_3$, 400MHz, TMS Int. St.)<br>δ: 1.25(3H, t), 1.59(8H, br), 2.57~2.64(6H, m), 2.95~3.00(2H, m), 3.75(2H, s), 4.20(2H, q), 4.50~4.60(1H, br), 5.02(1H, dd), 5.42(1H, d), 6.31(1H, d), 6.59(1H, d), 6.69(1H, d), 7.19~7.22(3H, m), 7.27~7.31(2H, m) |
| 48 | 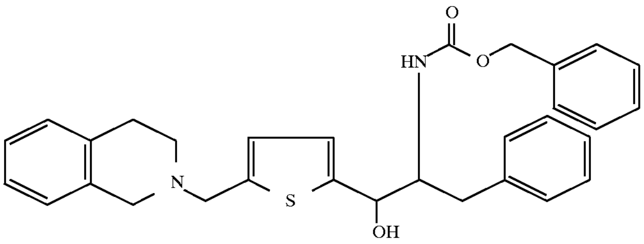 | MS(m/z): FAB Pos. 333($M^+$ + 1, 40%)<br>Anal: (for $C_{18}H_{24}N_2O_2s.⅓C_4H_6O_6.H_2O$)<br>C (%) H (%) N (%) S (%)<br>Calcd. 50.92 6.23 5.09 5.83<br>Measured 50.57 6.65 4.88 6.00<br>$^1$H-NMR(400MHz, DMSO, TMS Int. St.)<br>δ: 2.5(3H, s), 2.72~2.73(2H, m), 2.80~2.82(2H, m), 3.12~3.17(1H, m) 3.31~3.35(1H, m), 3.52~3.93(2H, m), 3.82~3.83(2H, m), 3.93(2H, s), 4.93~5.15(1H, m), 6.90~7.11(6H, m) |
| 49 | 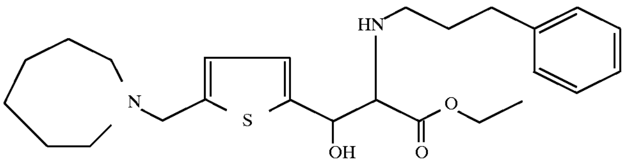 | MS(m/z): FAB (CI.) 445($M^+$ + 1, 10%)<br>$^1$H-NMR(400MHz, $CDCl_3$, TMS Int. St.)<br>δ: 1.09~1.24(3H, m), 1.52~1.80(8H, m), 1.78~1.95(2H, m), 2.47~2.74(8H, m), 3.32(1H, d, J=7.3Hz), 3.80(2H, s), 4.04~4.21(2H, m), 4.04~4.21(2H, m), 4.79(1H, d, J=7.3Hz), 6.68~6.78(2H, m), 7.15~7.29(5H, m) |

TABLE 25

| Ex. No. | Structural Formula | Physicochemical Properties |
|---|---|---|
| 50 | 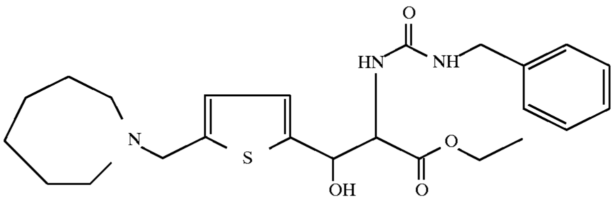 | MS(m/z): ZAB-SE FAB + 460.5($M^+$ + 1, 95%)<br>$^1$H-NMR(400MHz, $CDCl_3$, TMS Int. St.)<br>δ: 1.17(3H, t, J=7.0Hz), 1.51~1.66(8H, m), 4.04(2H, q, J=7.0Hz), 4.32~4.35(2H, m), 4.91~4.94(1H, m), 5.35(1H, d, J=3.4Hz), 5.55(1H, br), 5.67(1H, br) 6.65~6.68(2H, m), 7.21~7.32(5H, m) |

TABLE 25-continued

| Ex. No. | Structural Formula | Physicochemical Properties |
|---|---|---|
| 51 | 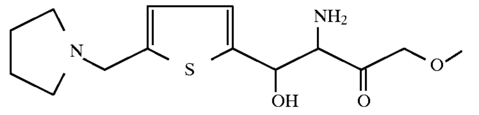 | MS(m/z): HR-MS for $C_{16}H_{27}H_2O_3S$<br>Calcd. 327.174240<br>Measured 327.176219<br>$^1$H-NMR(400MHz, $CDCl_3$, TMS Int. St.)<br>δ: 1.20~1.27(3H, m), 1.71(4H, br), 1.95(4H, br), 3.22(4H, br), 4.13(1H, q), 4.20(1H, q), 4.36(2H, s), 4.0~5.5(3H, br), 5.22(0.5H, s), 5.40(0.5H, d), 6.89(0.5H, d), 6.97(0.5H, d), 7.28(1H, m) |

Formulation Example

Next, an example of the formulation of the compound of the present invention as a pharmaceutical preparation is described.

| Composition | | |
|---|---|---|
| | 30 mg tablet | |
| Example 13-(3) | 30 mg | |
| Lactose | 65 | |
| Corn Starch | 16 | |
| Hydroxypropylcellulose | | 4.5 |
| Carboxymethylcellulose Calcium | | 8.8 |
| Magnesium Stearate | 0.7 | |
| Total | 120 mg | |

Using a fluidized granulation coating apparatus, 150 g of the compound of Example 13-(3) was uniformly mixed with 325 g of lactose and 80 g of corn starch. Then, 225 g of 10% hydroxypropylcellulose solution was sprayed to form granules. After drying, the granules were passed through a 20 mesh screen, mixed with 19 g of carboxymethylcellulose calcium and 8.5 g of magnesium stearate and then made into tablets each weighing 120 mg using a rotary tabletting machine equipped with a punch of 7 mm×8.4 R.

We claim:

1. A serine derivative represented by formula (I)

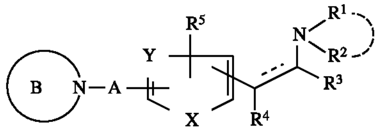

(I)

wherein

X is a sulfur atom or an oxygen atom,

Y is CH, $R^1$ and $R^2$ are the same or different from each other and each represents a hydrogen atom, a lower alkyl group or a protecting group for the amino group, $R^3$ is a carboxyl group, a protected carboxyl group, a phenyl-lower alkyl group, or a lower alkyl group substituted with a hydroxyl group, $R^4$ is a hydroxyl group, $R^5$ is a hydrogen atom or a lower alkyl group, A is a lower alkylene group,

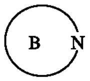

is a saturated four- to ten-membered ring containing a single nitrogen atom, and ... is a single bond, or a pharmaceutically acceptable salt thereof.

2. A serine derivative or pharmaceutically acceptable salt thereof according to claim 1, wherein the protecting group for the amino group in R1 or R2 is a lower alkoxycarbonyl group, a phenyl-lower alkoxy-carbonyl group or a phenyl-lower alkylaminocarbonyl group, the protected carboxyl group in R3 is a lower alkoxycarbonyl group.

3. 2-Amino-3-hydroxy-3-[5-(1-hexahydroazepinyl) methyl-2-thienyl]propionic acid or a pharmaceutically acceptable salt thereof.

4. Ethyl 2-benzyloxycarbonylamino-3-hydroxy-3-[5-(1-hexahydroazepinyl)methyl-2-thienyl]propionate or a pharmaceutically acceptable salt thereof.

5. Ethyl 2-benzyloxycarbonylamino-3-hydroxy-3-[5-(3-(1-hexahydroazepinyl)propyl)-2-thienyl]propionate or a pharmaceutically acceptable salt thereof.

6. Ethyl 2-benzylaminocarbonylamino-3-hydroxy-3-[5-(1-hexahydroazepinylmethyl)-2-thienyl]propionate or a pharmaceutically acceptable salt thereof.

7. A pharmaceutical composition which comprises as an active ingredient an effective amount of the serine derivative or pharmaceutically acceptable salt thereof according to claim 1, and a pharmaceutically acceptable carrier.

8. A method of treating a disease indicating symptoms induced by PCP, which comprises administering to a patient in need thereof an effective amount of a compound or a pharmaceutically acceptable salt of the serine derivative of claim 1.

9. A method as claimed in claim 8 wherein the disease is schizophrenia, dementia, Alzheimer's disease, problematic behavior caused by delirium, juvenile mental retardation or autism.

* * * * *